(12) United States Patent
Ebright

(10) Patent No.: US 8,114,583 B2
(45) Date of Patent: Feb. 14, 2012

(54) SWITCH-REGION: TARGET AND METHOD FOR INHIBITION OF BACTERIAL RNA POLYMERASE

(75) Inventor: Richard H. Ebright, Noth Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 29 days.

(21) Appl. No.: 12/612,787

(22) Filed: Nov. 5, 2009

(65) Prior Publication Data

US 2010/0311074 A1 Dec. 9, 2010

Related U.S. Application Data

(63) Continuation of application No. 11/351,709, filed on Feb. 10, 2006, now abandoned.

(60) Provisional application No. 60/651,227, filed on Feb. 10, 2005.

(51) Int. Cl.
*C12Q 1/00* (2006.01)
*G01N 33/53* (2006.01)

(52) U.S. Cl. ............................... 435/4; 435/7.1; 435/7.6

(58) Field of Classification Search ........................ None
See application file for complete search history.

(56) References Cited

FOREIGN PATENT DOCUMENTS

WO    WO 2004/023093    *    3/2004

OTHER PUBLICATIONS

Irschik et al (The Journal of Antibiotics vol. XXXXVI, No. 12, 1983).*

* cited by examiner

*Primary Examiner* — Oluwatosin Ogunbiyi

(57) ABSTRACT

A target and methods for specific binding and inhibition of RNA polymerase from bacterial species are provided, including methods for identifying agents that bind to a bacterial RNA polymerase, and that inhibit an activity of a bacterial RNA polymerase, through interactions with a bacterial RNA polymerase homologous switch-region amino-acid sequence. The methods can include preparation of a reaction solution comprising the compound to be tested and an entity containing a bacterial RNAP homologous switch-region amino-acid sequence, and detection of binding or inhibition. Applications in control of bacterial gene expression, control of bacterial viability, control of bacterial growth, antibacterial chemistry, and antibacterial therapy are also provided.

55 Claims, 10 Drawing Sheets
(6 of 10 Drawing Sheet(s) Filed in Color)

SWITCH-REGION: TARGET AND METHOD FOR INHIBITION OF BACTERIAL RNA POLYMERASE

CROSS-REFERENCE TO RELATED APPLICATIONS

This application claims priority to provisional application: 60/651,227 filed Feb. 10, 2005, the contents of which are incorporated herein by reference.

GOVERNMENT SUPPORT

This invention was supported with U.S. Government funds (NIH RO1-GM41376). Therefore, the Government may have rights in the invention.

BACKGROUND ART

Bacterial infections remain among the most common and deadly causes of human disease. Infectious diseases are the third leading cause of death in the United States and the leading cause of death worldwide (Binder et al. (1999) *Science* 284, 1311-1313). Multi-drug-resistant bacteria now cause infections that pose a grave and growing threat to public health. It has been shown that bacterial pathogens can acquire resistance to first-line and even second-line antibiotics (Stuart B. Levy, The Challenge of Antibiotic Resistance, in Scientific American, 46-53 (March, 1998); Walsh, C. (2000) *Nature* 406, 775-781; Schluger, N. (2000) *Int. J. Tuberculosis Lung Disease* 4, S71-S75; Raviglione et al., (2001) *Ann. NY Acad. Sci.* 953, 88-97). New approaches to drug development are necessary to combat the ever-increasing number of antibiotic-resistant pathogens.

The present invention provides one such approach.

RNA polymerase (RNAP) is the molecular machine responsible for transcription and is the target, directly or indirectly, of most regulation of gene expression (Ebright, R. (2000) *J. Mol. Biol.* 304, 687-698; Darst, S. (2001) *Curr. Opin. Structl. Biol.* 11, 155-162; Cramer, P. (2002) *Curr. Opin. Structl. Biol.* 12, 89-97; Murakami & Darst (2003) *Curr. Opin. Structl. Biol.* 13, 31-39; Borukhov & Nudler (2003) *Curr. Opin. Microbiol.* 6, 93-100; Landick, R. (2001) *Cell* 105, 567-570; Korzheva & Mustaev (2001) *Curr. Opin. Microbiol.* 4, 119-125; Armache, et al. (2005) *Curr. Opin. Structl. Biol.* 15, 197-203; Woychik & Hampsey (2002); *Cell* 108, 453-463; Asturias, F. (2004) *Curr. Opin. Genet Dev.* 14, 121-129; Cramer, P. (2004) *Curr. Opin. Genet. Dev.* 14, 218-226; Geiduschek & Kassayetis (2001) *J. Mol. Biol.* 310, 1-26). Bacterial RNAP core enzyme has a molecular mass of ~380,000 Da and consists of one β' subunit, one β subunit, two α subunits, and one ω subunit; bacterial RNAP holoenzyme has a molecular mass of ~450,000 Da and consists of bacterial RNAP core enzyme in complex with the transcription initiation factor σ (Ebright, R. (2000) *J. Mol. Biol.* 304, 687-698; Darst, S. (2001) *Curr. Opin. Structl. Biol.* 11, 155-162; Cramer, P. (2002) *Curr. Opin. Structl. Biol.* 12, 89-97; Murakami & Darst (2003) *Curr. Opin. Structl. Biol.* 13, 31-39; Borukhov & Nudler (2003) *Curr. Opin. Microbiol.* 6, 93-100). Bacterial RNAP core subunit sequences are conserved across Gram-positive and Gram-negative bacterial species (Ebright, R. (2000) *J. Mol. Biol.* 304, 687-698; Darst, S. (2001) *Curr. Opin. Structl. Biol.* 11, 155-162; Iyer, et al. (2004) *Gene* 335, 73-88). Eukaryotic RNAP I, RNAP II, and RNAP III contain counterparts of all bacterial RNAP core subunits, but eukaryotic-subunit sequences and bacterial-subunit sequences exhibit only limited conservation (Ebright, R. (2000) *J. Mol. Biol.* 304, 687-698; Darst, S. (2001) *Curr. Opin. Structl. Biol.* 11, 155-162; Cramer, P. (2002) *Curr. Opin. Structl. Biol.* 12, 89-97).

Bacterial RNAP is a proven target for antibacterial therapy (Chopra, et al. (2002) *J. Appl. Microbiol.* 92, 4S-15S; Darst, S. (2004) *Trends Biochem. Sci.* 29, 159-162). The suitability of bacterial RNAP as a target for antibacterial therapy follows from the fact that bacterial RNAP is an essential enzyme (permitting efficacy), the fact that bacterial RNAP subunit sequences are conserved (providing a basis for broad-spectrum activity), and the fact that bacterial RNAP subunit sequences are only weakly conserved in eukaryotic RNAP I, RNAP II, and RNAP III (providing a basis for therapeutic selectivity).

The rifamycin antibacterial agents—notably rifampicin, rifapentine, and rifabutin—function by binding to and inhibiting bacterial RNAP (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). The rifamycins bind to a site on bacterial RNAP adjacent to the RNAP active center and sterically and/or allosterically prevent extension of RNA chains beyond a length of 2-3 nt (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). The rifamycins are in current clinical use in treatment of Gram-positive and Gram-negative bacterial infections (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). The rifamycins are of particular importance in treatment of tuberculosis; the rifamycins are first-line anti-tuberculosis agents and are the only anti-tuberculosis agents able rapidly to clear infection and prevent relapse (Mitchison, D. (2000) *Int. J. Tuberc. Lung Dis.* 4, 796-806). The rifamycins also are of importance in treatment of bacterial infections relevant to biowarfare or bioterrorism; combination therapy with ciprofloxacin, clindamycin, and rifampicin was successful in treatment of inhalational anthrax following the 2001 anthrax attacks (Mayer, et al. (2001) *JAMA* 286, 2549-2553), and combination therapy with ciprofloxacin and rifampicin, or doxycycline with rifampicin, is recommended for treatment of future cases of inhalational anthrax (Centers for Disease Control and Prevention (2001) *JAMA* 286, 2226-2232).

The clinical utility of the rifamycin antibacterial agents is threatened by the existence of bacterial strains resistant to rifamycins (Chopra, et al. (2002) *J. Appl. Microbiol.* 92, 4S-15S; Darst, S. (2004) *Trends Biochem. Sci.* 29, 159-162; Floss & Yu (2005) *Chem. Rev.* 105, 621-632; Campbell, et al. (2001) *Cell* 104, 901-912; Artsimovitch, et al. (2005) *Cell* 122, 351-363). Resistance to rifamycins typically involves substitution of residues in or immediately adjacent to the rifamycin binding site on bacterial RNAP—i.e., substitutions that directly decrease binding or function of rifamycins. A significant and increasing percentage of cases of tuberculosis are resistant to rifampicin (1.4% of new cases, 8.7% of previously treated cases, and 100% of cases designated multi-drug-resistant, in 1999-2002; Schluger, N. (2000) *Int. J. Tuberc. Lung Dis.* 4, S71-S75; Raviglione, et al. (2001) *Ann. N.Y. Acad. Sci.* 953, 88-97; Zumia, et al. (2001) *Lancet Infect. Dis.* 1, 199-202; Dye, et al. (2002) *J. Infect. Dis.* 185, 1197-1202; WHO/IUATLD (2003) *Anti-tuberculosis drug resistance in the world: third global report* (WHO, Geneva)).

Strains of bacterial bioweapons agents resistant to rifampicin can be, and have been, constructed (Lebedeva, et al. (1991) *Antibiot. Khimioter.* 36, 19-22; Pomerantsev, et al. (1993) *Antibiot. Khimioter.* 38, 34-38; Volger, et al. (2002) *Antimicrob. Agents Chemother.* 46, 511-513; Marianelli, et al. (204) *J. Clin. Microbiol.* 42, 5439-5443).

In view of the public-health threat posed by rifamycin-resistant and multidrug-resistant bacterial infections, there is an urgent need for new classes of antibacterial agents that (i) target bacterial RNAP (and thus have the same biochemical effects as rifamycins), but that (ii) target sites within bacterial RNAP distinct from the rifamycin binding site (and thus do not show cross-resistance with rifamycins). (See Chopra, et al. (2002) *J. Appl. Microbiol.* 92, 4S-15S; Darst, S (2004) *Trends Biochem. Sci.* 29, 159-162.)

Recently, crystallographic structures have been determined for bacterial RNAP and eukaryotic RNAP II (Zhang et al., (1999) *Cell* 98, 811-824; Cramer et al., (2000) *Science* 288, 640-649; Naryshkin et al., (2000) *Cell* 101, 601-611; Kim et al., (2000) *Science* 288, 1418-1421; Korzheva et al., (2000) *Science* 289, 619-625; Ebright, R. (2000) *J. Mol. Biol.* 304, 687-689; Cramer et al., (2001) *Science* 292, 1863-1876; Gnatt et al., (2001) *Science* 292, 1876-1882; Mekler et al., (2002) *Cell* 108, 599-614; Murakami et al., (2002) *Science* 296, 1280-1284; Murakami et al., (2002) *Science* 296, 1285-1290; Vassylyev et al., (2002) *Nature* 417, 712-719; Bushnell et al., (2004) *Science* 303, 983-988; Westover et al., (2004) *Science* 303, 1014-1016; Armache, et al., (2003) *Proc. Natl. Acad. Sci. USA* 100, 6964-6968). Moreover, cryo-EM structures have been determined for bacterial RNAP and eukaryotic RNAP I (Opalka, et al. (2000) *Proc. Natl. Acad. Sci. USA* 97, 617-622; Darst, et al. (2002) *Proc. Natl. Acad. Sci. USA* 99, 4296-4301; DeCarlo, et al. (2003) *J. Mol. Biol.* 329, 891-902).

Structures also have been determined for RNAP complexes with nucleic acids, nucleotides and inhibitors (Campbell, et al. (2001) *Cell* 104, 901-912; Artsimovitch, et al. (2005) *Cell* 122, 351-363; Campbell, et al. (2005) *EMBO J.* 24, 674-682; Artsimovitch, et al. (2004) *Cell* 117, 299-310; Tuske, et al. (2005) *Cell* 122, 541-522; Temiaov, et al. (2005) *Mol. Cell.* 19, 655-666; Vassulyev, et al. (2005) *Nature Structl. Biol.* 12, 1086-1093; Gnatt, et al. (2001) *Science* 292, 1876-1882; Westover, et al. (2004a) *Science* 303, 1014-1016; Westover, et al. (2004b) *Cell* 119, 481-489; Ketenberger, et al. (2004) *Mol. Cell.* 16, 955-965; Bushnell, et al. (2002) *Proc. Natl. Acad. Sci. U.S.A.* 99, 1218-1222; Kettenberger, et al. (2005) *Natl. Structl. Mol. Biol.* 13, 44-48).

The structures reveal that RNAP-bacterial or eukaryotic—has a shape reminiscent of a crab claw. The two "pincers" of the "claw" define the active-center cleft that can accommodate a double-stranded nucleic acid—and which has the active-center $Mg^{2+}$ at its base (FIG. 1A). The largest submit (β' in bacterial RNAP) makes up one pincer, termed the "clamp," and part of the base of the active-center cleft. The second-largest subunit (β in bacterial RNAP) makes up the other pincer and part of the base of the active-center cleft.

The structures further reveal that the RNAP clamp can exist in a range of distinct conformational states—from a fully open clamp conformation that permits unimpeded entry and exit of DNA to a fully closed clamp conformation that prevents entry and exit of DNA (FIG. 1A; Ebright (2000) *J. Mol. Biol.* 304, 687-698; Darst (2001) *Curr. Opin. Structl. Biol.* 11, 155-162; Cramer (2002) *Curr. Opin. Structl. Biol.* 12, 89-97; Murakami & Darst (2003) *Curr. Opin. Structl. Biol.* 13, 31-39; Borukhob & Nudler (2003) *Curr. Opin. Microbiol.* 6, 93-100; and Landick (2001) *Cell* 105, 567-570). It has been proposed that the clamp opens to permit DNA to enter the active-center cleft in transcription initiation, closes after DNA enters the active-center cleft in transcription initiation, and further closes, or acquires further stability in the closed state, in transcription elongation. Clamp closure is proposed to be responsible for the high stability of initiation complexes and for the exceptionally high stability and exceptionally high processivity of elongation complexes.

The "switch region" is located at the base of the clamp (FIG. 1A). The switch region serves as a hinge that permits rotation of the β' "pincer" relative to the remainder of RNAP, and, correspondingly, permits opening or closing of the RNA-Pactive-center cleft. The switch region adopts different conformations when the β' pincer is rotated out of the active-center cleft (open-clamp state, required for entry of DNA into active-center cleft) and when the β' is rotated into the active-center cleft (closed-clamp state, required for stable binding of DNA within active-center cleft) (FIG. 1B; Cramer (2002) *Curr. Opin. Structl. Biol.* 12, 89-97; Landick (2001) *Cell* 105, 567-570; Cramer, et al. (2001) *Science* 292, 1863-1876; Gnatt, et al. (2001) *Science* 292, 1876-1882).

Several residues of the switch region make direct contacts with DNA phosphates in the transcription elongation complex (Gnatt, et al. (2001) *Science* 292, 1876-1882; Westover, et al. (2004a) *Science* 303, 1014-1016; Westover, et al. (2004a) *Science* 303, 1014-1016; Westover, et al. (2004b) *Cell* 119, 481-489; Kettenberger, et al. (2004) *Mol. Cell.* 16, 955-965). Furthermore, it has been proposed that direct contents between the switch region and DNA phosphates might coordinate, and even might mechanically couple, clamp closure and DNA binding (Cramer, et al. (2002) *Curr. Opin. Structl. Biol.* 12 89-97; Landick, et al. (2001) *Cell* 105, 567-570; Cramer, et al. (2001) *Science* 292, 1863-1876; and Gnatt, et al. (2001) *Science* 292, 1876-1882).

SUMMARY OF THE INVENTION

Applicant has discovered a target, located within the bacterial RNAP switch region, through which small molecules are able to bind to bacterial RNAP, to inhibit bacterial RNAP, and to inhibit bacterial growth (FIGS. 2,3). The target comprises four short segments of the bacterial RNAP β' and β subunits (FIG. 3). The target comprises residues that correspond to, and are alignable with, residues 345 and 1351 of the β' subunit of RNAP from *Escherichia coli* and residues 1275-1292 and 1322-1326 of the β subunit of RNAP from *Escherichia coli* (FIG. 3). Throughout the following specification, said target is referred to as the "switch-region target," and said four short segments collectively are referred to as the "homologous switch-region amino-acid sequence."

Applicant's results establish that the switch-region target is an exceptionally attractive target for drug discovery: (1) The switch-region target involves a critical structural element of bacterial RNAP (a structural element proposed to mediate conformation changes required for RNAP to bind to and retain the DNA template in transcription), providing a basis for efficient inhibition of bacterial RNAP and bacterial growth. (2) The switch-region target is conserved in Gram-positive and Gram-negative bacterial RNAP, providing a basis for broad-spectrum activity. (3) The switch-region target contains residues that are not conserved in human RNAP I, RNAP II, and RNAP III, providing a basis for therapeutic selectivity. (4) The switch-region target is remote from the binding site for the RNAP inhibitors in current clinical use (rifamycins), providing a basis for complete absence of cross-resistance with the RNAP inhibitors in current clinical use. (5) Applicant has identified three natural products that bind to the switch-region target, inhibit bacterial RNAP through the switch-region target, and inhibit bacterial growth through the switch-region target—providing examples of switch-region-target-dependent inhibitors. (6) Applicant and Applicant's co-workers have determined a high-resolution crystal structure of a complex of RNAP with one natural product that binds to the switch-region target, inhibits bacterial RNAP through the switch-region target, and inhibits bacterial growth through the switch-region target—enabling structure-based screening for new switch-region-target-dependent inhibitors. (7) Applicant has developed binding, enzymatic-activity, and antibacterial-activity assays for small molecules that bind to the switch-region target, inhibit bacterial RNAP through the switch-region target, and inhibit bacterial growth through the switch-region target—enabling de novo screening for new switch-region-target-dependent inhibitors.

Applicant has discovered that a sub-region within the bacterial RNAP switch region comprising four short segments of the RNAP β' and β subunits is conserved in amino-acid sequence in bacterial, species, including both Gram-positive bacterial species and Gram-negative bacterial species. The four short segments correspond to, and are alignable with, residues 345 and 1351 of the β' subunit of RNAP from *Escherichia coli* and residues 1275-1292 and 1322-1326 of the β subunit of RNAP from *Escherichia coli*. Applicant further has discovered that this sub-region is not conserved, and in fact is radically different, in amino-acid sequence in eukaryotic RNAP, including human RNAP I, human RNAP II, and human RNAP III. Applicant further has discovered that this target forms a discrete pocket, located in the center of the switch region, in the three-dimensional structure of bacterial RNAP.

Accordingly, a first aspect of the present invention is directed to a method for identifying agents that bind to a bacterial RNAP homologous switch-region amino-acid sequence, comprising preparing a reaction solution including the agent to be tested and an entity containing a bacterial-RNAP homologous switch-region amino-acid sequence; and detecting the presence or amount of binding to the bacterial-RNAP homologous switch-region amino-acid sequence. In a preferred embodiment, detection or quantitation of binding is conducted relative to binding of the agent to an entity containing an altered bacterial-RNAP homologous switch-region amino-acid sequence.

Another aspect of the present invention is directed to a method for identifying agents that inhibit an activity of bacterial RNAP via binding to a bacterial-RNAP homologous switch-region amino-acid sequence. This aspect entails preparing a reaction solution including the agent to be tested, an entity containing a bacterial-RNAP homologous switch-region amino-acid sequence, and a substrate for the entity; and determining the extent of inhibition of an activity of the entity via binding of the agent to the bacterial-RNAP homologous switch-region amino-acid sequence. In a preferred embodiment, detection or quantitation of inhibition is conducted relative to inhibition by the agent of an entity containing an altered bacterial-RNAP homologous switch-region amino-acid sequence.

Another aspect of the present invention is directed to a method for identifying agents that inhibit at least one of bacterial viability and bacterial growth via binding to a bacterial-RNAP homologous switch-region amino-acid sequence. This aspect entails contacting a bacterium with the agent to be tested, and determining the extent of inhibition of at least one of bacterial viability and bacterial growth. In a preferred embodiment, detection or quantitation of inhibition is conducted relative to inhibition by the agent of viability or growth of a bacterium containing an altered bacterial-RNAP homologous switch-region amino-acid sequence.

In some preferred embodiments, binding or inhibition is compared to binding or inhibition by myxopyronin (Myx), corallopyronin (Cor), or ripostatin (Rip). Applicant has discovered that each of these compounds inhibits bacterial RNAP through interaction with the bacterial-RNAP homologous switch-region amino-acid sequence. Applicant's results indicate that Myx, Cor, and Rip interact with residues that are conserved in Gram-positive and Gram-negative bacterial RNAP and, accordingly, exhibit broad-spectrum antibacterial activity. Applicant's results indicate that Myx, Cor, and Rip interact, in part, with residues that are not conserved in eukaryotic RNAP I, RNAP II, and RNAP III, and, accordingly, do not exhibit cross-inhibition of eukaryotic RNAP. Applicant's results further indicate that Myx, Cor, and Rip interact with residues that are remote from the binding sites for rifamycins and other characterized RNAP inhibitors, and, accordingly, do not exhibit cross-resistance with rifamycins and other characterized RNAP inhibitors. Applicant's results further indicate that Myx, Cor, and Rip may function by inhibiting switch-region conformational cycling, thereby preventing the opening of the RNAP clamp required for DNA binding and/or the closing of the RNAP clamp required for DNA retention. Taken together, these properties render Myx, Cor, and Rip exceptionally attractive candidates for development as antibacterial therapeutic agents.

The present invention provides that each of Myx, Cor, and Rip inhibits bacterial RNAP by binding to a determinant that includes residues within the bacterial RNAP homologous switch-region amino-acid sequence.

The present invention also provides for the identification of potential antibacterial agents that, because they interact with residues that are conserved in bacterial RNAP, have broad-spectrum antibacterial activity. The invention also provides for the identification of potential antibacterial agents that, because they interact, in part, with residues that are not conserved in eukaryotic RNAP, are relatively non-disruptive to normal cellular functions of eukaryotes.

The invention also provides for the identification of potential antibacterial agents that, because they interact with residues that are remote from the binding sites for rifamycins and other characterized RNAP inhibitors, do not exhibit cross-resistance with rifamycins and other characterized RNAP inhibitors.

It is anticipated that compounds identified according to the target and method of this invention would have applications not only in antibacterial therapy, but also in: (a) identification of bacterial RNAP (diagnostics, environmental-monitoring, and sensors applications); (b) labeling of bacterial RNAP (diagnostics, environmental-monitoring, imaging, and sensors applications); (c) immobilization of bacterial RNAP (diagnostics, environmental-monitoring, and sensors applications); (d) purification of bacterial RNAP (biotechnology applications); (e) regulation of bacterial gene expression (biotechnology applications); and (f) antisepsis (antiseptics, disinfectants, and advanced-materials applications).

These and other aspects of the present invention will be better appreciated by reference to the following drawings and Detailed Description.

The file of this patent contains at least one drawing executed in color. Copies of this patent with color drawing(s) will be provided by the Patent and Trademark Office upon request and payment of the necessary fee.

BRIEF DESCRIPTION OF THE DRAWINGS

FIG. 3 shows sequence alignments of the bacterial RNAP homologous switch-region amino-acid sequences (red boxes) from *Escherichia coli* (SEQ ID NOS: 1, 2, 4 and 5), *Haemophilus influenzae* (SEQ ID NOS: 6, 7, 9 and 10), *Vibrio cholerae* (SEQ ID NOS: 11, 12, 14 and 15), *Pseudomonas aeruginosa* (SEQ ID NOS: 16, 17, 19 and 20), *Treponema pallidum* (SEQ ID NOS: 21, 22, 24 and 25), *Borrelia burgdorferi* (SEQ ID NOS: 26, 27, 29 and 30), *Xyella fastidiosa* (SEQ ID NOS: 31, 32, 34 and 35), *Campylobacter jejuni* (SEQ ID NOS: 36, 37, 39 and 40), *Neisseria meningitides* (SEQ ID NOS: 41, 42, 44 and 45), *Rickettsia prowazekii* (SEQ ID NOS: 46, 47, 49 and 50), *Chlamydia trachomatis* (SEQ ID NOS: 51, 52, 54 and 55), *Mycoplasma pneumoniae* (SEQ ID NOS: 56, 57, 59 and 60), *Bacillus subtilis* (SEQ ID NOS: 61, 62, 64 and 65), *Staphylococcus aureus* (SEQ ID NOS: 66, 67, 69 and 70), *Mycobacterium tuberculosis* (SEQ ID NOS: 71, 72, 74 and 75), *Synechocystis* sp. (SEQ ID NOS: 76, 77, 79 and 80), *Aquifex aeolicus* (SEQ ID NOS: 81, 82, 84 and 85), *Deinococcus radiodurans* (SEQ ID NOS: 86, 87, 89 and 90), *Thermus thermophilus* (SEQ ID NOS: 91, 92, 94 and 95), and *Thermus aquaticus* (SEQ ID NOS: 96, 97, 99 and 100); and of the corresponding residues of human RNAP I (SEQ ID NOS: 101, 102, 104 and 105), RNAP II (SEQ ID NOS: 106, 107, 109 and 110), and RNAP III (SEQ ID NOS: 111, 112, 114 and 115). Sequences for bacterial RNAP are at top; sequences for human RNAP I, RNAP II, and RNAP III are at bottom. The sequence alignments include both the bacterial RNAP homologous switch-region amino-acid sequences and the adjacent flanking sequences; the bacterial RNAP homologous switch-region amino-acid sequences are indicated by red boxes. (A) Sequences of β' subunits of bacterial RNAP and largest subunits of human RNAP I, RNAP II, and RNAP III. (B) Sequences of β subunits of bacterial RNAP and second-largest subunits of human RNAP I, RNAP II, and RNAP III.

FIG. 6 shows sequence alignments for segments of *Escherichia coli* β' subunit (A) and β subunit (B) in which single-residue substitutions conferring Myx-resistance are obtained (sites of high-level resistance boxed in red; sites of moderate-level resistance boxed in black). Sequences for bacterial RNAP from *Escherichia coli* (SEQ ID NOS: 1-5), *Haemophilus influenzae* (SEQ ID NOS: 6-10), *Vibrio cholerae* (SEQ ID NOS: 11-15), *Pseudomonas aeruginosa* (SEQ ID NOS: 16-20), *Treponema pallidum* (SEQ ID NOS: 21-25), *Borrelia burgdorferi* (SEQ ID NOS: 26-30), *Xyella fastidiosa* (SEQ ID NOS: 31-35), *Campylobacter jejuni* (SEQ ID NOS: 36-40), *Neisseria meningitides* (SEQ ID NOS: 41-45), *Rickettsia prowazekii* (SEQ ID NOS: 46-50), *Chlamydia trachomatis* (SEQ ID NOS: 51-55), *Mycoplasma pneumoniae* (SEQ ID NOS: 56-60), *Bacillus subtilis* (SEQ ID NOS: 61-65), *Staphylococcus aureus* (SEQ ID NOS: 66-70), *Mycobacterium tuberculosis* (SEQ ID NOS: 71-75), *Synechocystis* sp. (SEQ ID NOS: 76-80), *Aquifex aeolicus* (SEQ ID NOS: 81-85), *Deinococcus radiodurans* (SEQ ID NOS: 86-90), *Thermus thermophilus* (SEQ ID NOS: 91-95), and *Thermus aquaticus* (SEQ ID NOS: 96-100) are at top; sequences for human RNAP I (SEQ ID NOS: 101-105), RNAP 11 (SEQ ID NOS: 106-110), and RNAP III (SEQ ID NOS: 111-115) are at bottom.

BEST MODE OF CARRYING OUT THE INVENTION

The present invention provides methods of designing specific inhibitors of bacterial RNAP, the enzyme responsible for transcription. The invention provides targets and methods for specific binding and inhibition of bacterial RNAP. The invention has applications in control of bacterial gene expression, control of bacterial growth, antibacterial chemistry, and antibacterial therapy.

Figure 1:
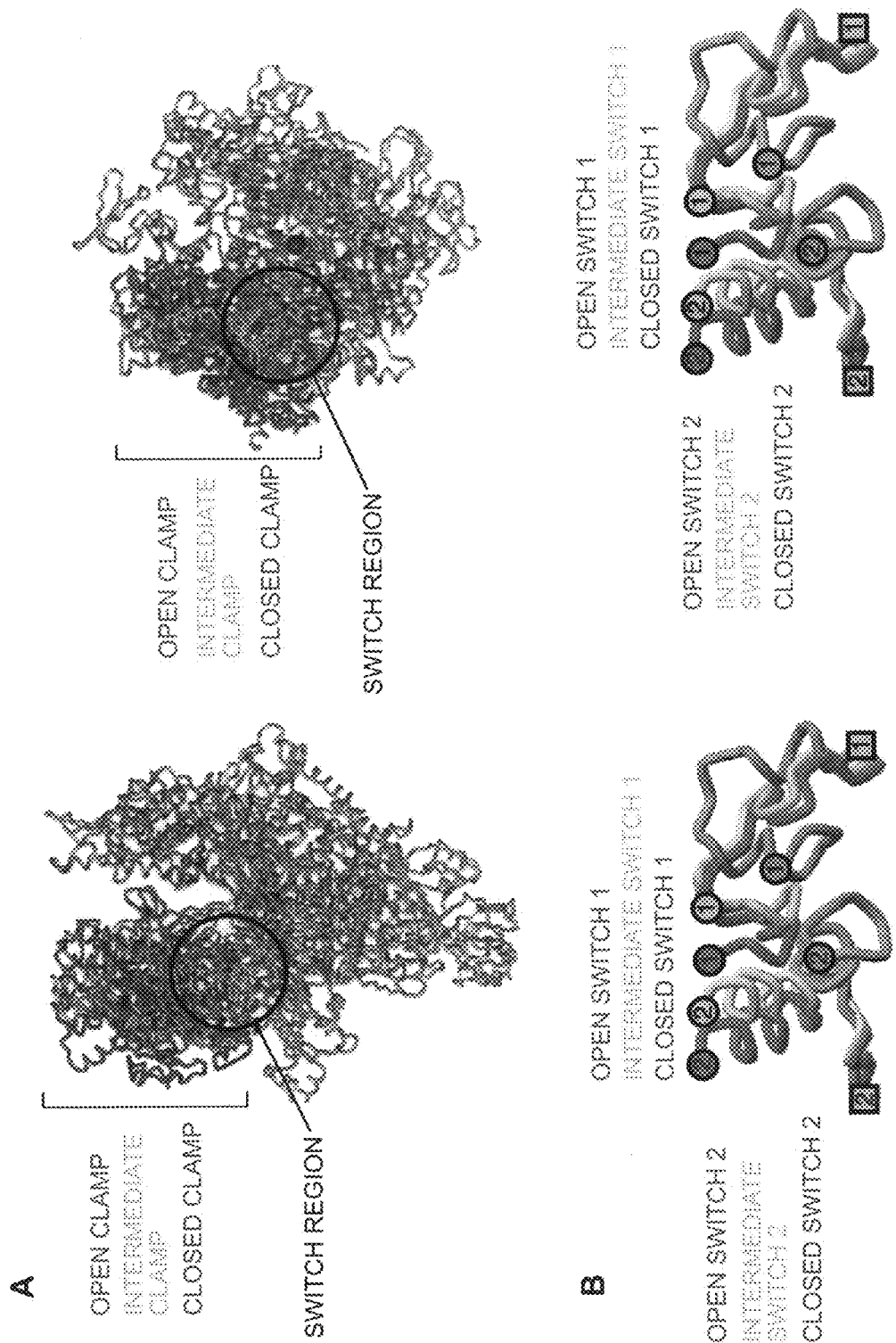
FIG. 1 illustrates the three-dimensional structure of bacterial RNAP (β' nonconserved domain and σ omitted for clarity). (A) Structure of RNAP, showing open (red), intermediate (yellow) and closed (green) clamp conformations, as observed in crystal structures; violet sphere, active-center $Mg^{2+}$. Two orthogonal views are shown: at left, a view through the RNAP active-center cleft; at right, a view directly into the RNAP active-center cleft. (B) Structure of RNAP switch-region, showing open (red), intermediate (yellow) and closed (green) clamp conformations, as observed in crystal structures. A stereoview is shown of the structural elements known as "switch 2" and "switch 1" (β' residues 330-349 and 1304-1329; residues numbered as in *Escherichia coli* RNAP). Gray squares, points of connection of switch 2 and switch 1 to the RNAP main mass; colored circles, points of connection of switch 2 and switch 1 to the RNAP clamp.

As described above, structural information for bacterial RNAP implies that the RNAP switch region serves as a hinge that permits rotation of the β' subunit (termed the "clamp") relative to the remainder of RNAP, and correspondingly, that permits opening or closing of the RNAP active-center cleft (FIG. 1A). The clamp is proposed to open to permit entry of DNA into the active-center cleft in transcription initiation. The clamp is proposed to close to permit stable retention of DNA within the active-center cleft in later steps of transcription initiation and in transcription elongation. In addition to serving as the hinge for the proposed opening and closing of the clamp in transcription initiation and elongation, the switch region is proposed to make direct contacts with DNA in transcription initiation and in transcription elongation. In summary, the switch region is proposed to play roles important for function of RNAP in transcription initiation and in transcription elongation.

It now has been found, and is disclosed herein, that binding of Myx, Cor, or Rip within the switch region inhibits transcription. Specifically, it has now been found, and is disclosed herein, that binding of Myx, Cor, or Rip within the switch region inhibits transcription by preventing stable interaction of RNAP with a promoter-DNA segment that binds with the RNAP active-center cleft.

Figure 2:
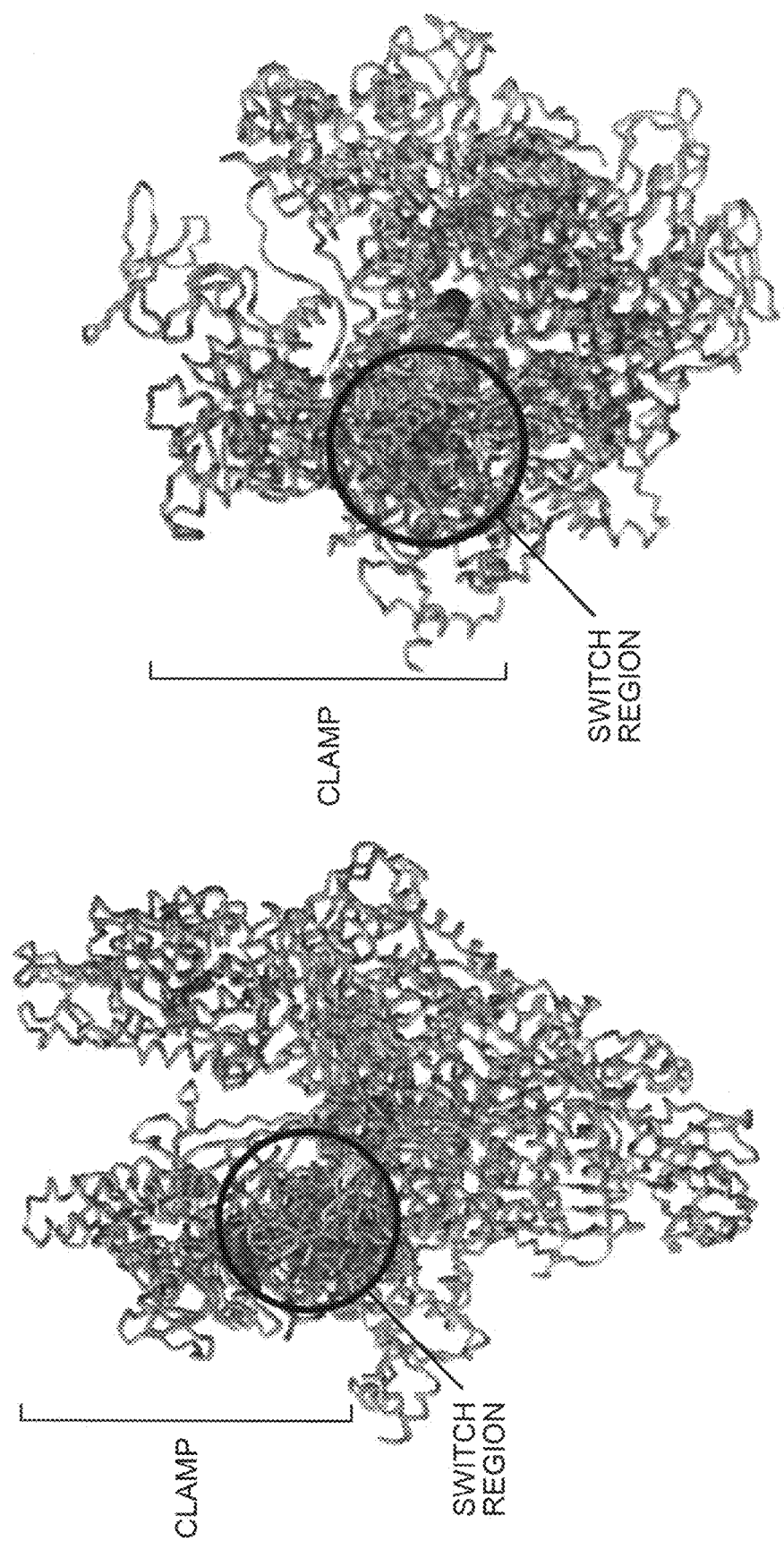
FIG. 2 illustrates the location of the bacterial RNAP homologous switch-region amino-acid sequence within the three-dimensional structure of bacterial RNAP (β' nonconserved domain and σ omitted for clarity). Red, residues of the bacterial RNAP homologous switch-region amino-acid sequence; violet sphere, active-center $Mg^{2+}$. Two orthogonal views are shown: at left, a view through the RNAP active-center cleft; at right, a view directly into the RNAP active-center cleft.
Figure 3:
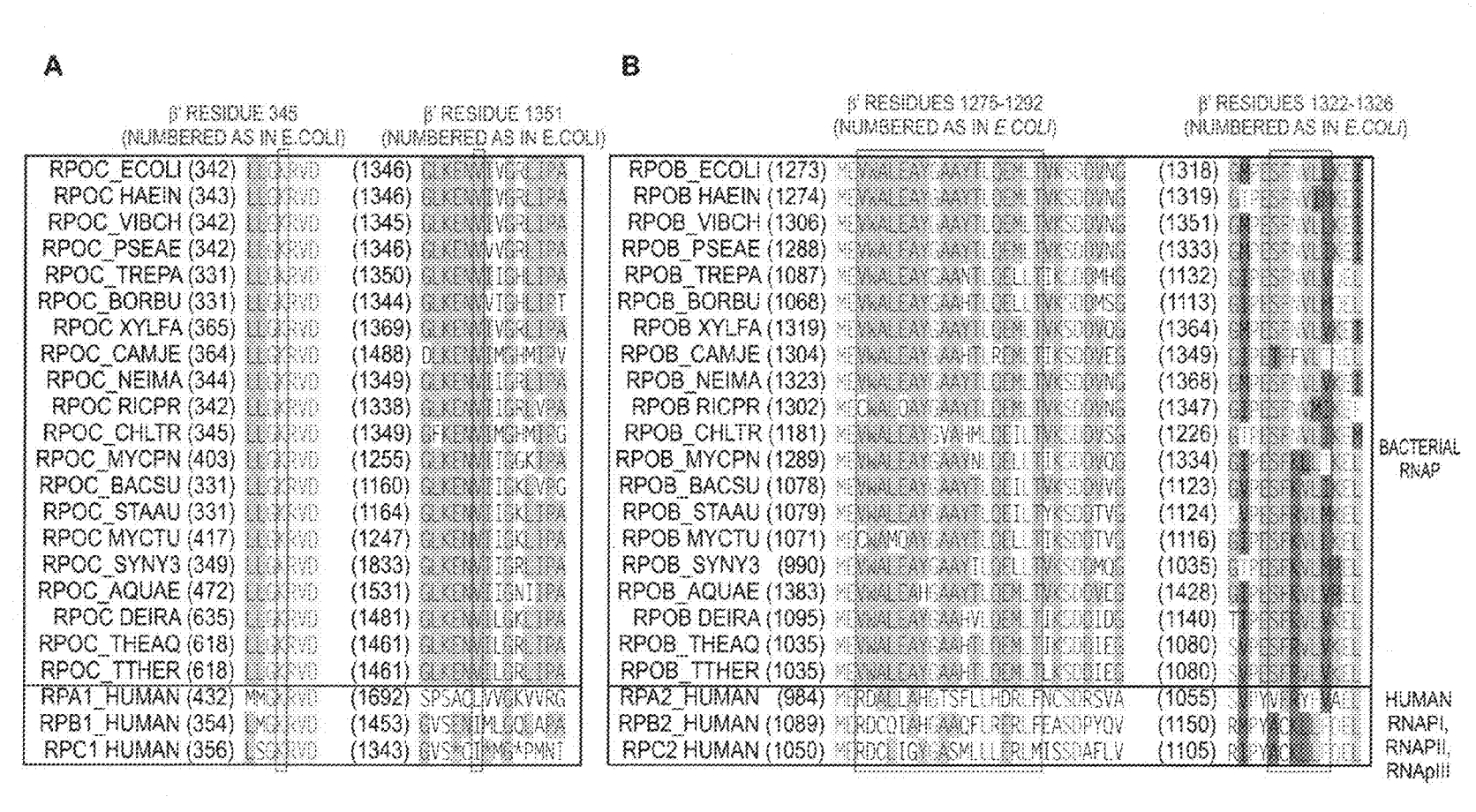

The present invention includes the discovery that a region within the bacterial RNAP switch region comprising residues corresponding to, and alignable with, residues 345 and 1351 of the β' subunit of RNAP from *Escherichia coli* and residues 1275-1292 and 1322-1326 of the β subunit of RNAP from *Escherichia coli* (the "switch-region target" or "homologous switch-region amino-acid sequence"; FIGS. 2,3) is a useful target for compounds that block transcription. It was found that residues of the bacterial RNAP homologous switch-region amino-acid sequence are invariant, or nearly invariant, in RNAP from bacterial species, but are, for at least in part, radically different in RNAP from eukaryotic species (FIG. 3). It further was found that, in the three-dimensional structure of bacterial RNAP, residues of the bacterial RNAP homologous switch-region amino-acid sequence form a discrete pocket, with dimensions of approximately 20×20×10 Å, located within the RNAP switch region (FIG. 2).

The location of the target within the bacterial RNAP switch region is such that binding to the target of a small molecule would be predicted to lock the switch region in one conformation—either a conformation of a open-clamp state, a conformation of an intermediate-clamp state, a conformation of a closed-clamp state, or an aberrant, small-molecule-dependent conformation. This would be predicted to prevent switch-region conformational cycling required for entry of DNA into the active-center cleft, for stable binding of DNA within the active-center cleft, or for both. The location of the target within the switch region also is such that binding to the target of a small molecule might be predicted to interfere with interactions between RNAP and DNA (either by inhibiting transcription through allosteric interactions or through steric clash with the DNA template strand).

The target referred to above is highly similar in amino-acid sequence in RNAP from most or all other species of bacteria and is referred to herein as the "switch-region target" or the "homologous switch-region amino-acid sequence" (FIGS. 2,3). (For example, residues 345 and 1351 of the β' subunit and residues 1275-1292 and 1322-1326 of the β subunit of RNAP from *Escherichia coli* correspond to, and are alignable with, residues 334 and 1165 of the β' subunit and residues 1080-1097 and 1127-1131 of the β subunit of RNAP from *Bacillus subtilis*; FIG. 3.) Thus, a molecule found to bind to the switch-region target and inhibit an activity associated with the switch-region target in RNAP from one species of bacteria, for example RNAP from *Escherichia coli*, is likely also to bind to the target and inhibit an activity associated with the switch-region target in RNAP from other species of bacteria. Likewise, a molecule found to have antibacterial activity (through binding to and inhibiting an activity associated with the switch-region target) against one species of bacteria, for example *Escherichia coli*, is likely to have antibacterial activity against other species of bacteria.

In contrast, the target is not similar, and in part differs radically, in amino acid sequence between bacterial RNAP and eukaryotic RNAP, including human RNAP I, human RNAP II, and human RNAP III (FIG. 3). This allows for the identification of molecules that bind in a switch-region-target-dependent fashion to bacterial RNAP, but that do not bind, or that bind substantially less well, to eukaryotic RNAP. This also allows for the identification of molecules that inhibit in a switch-region-target-dependent fashion an activity of bacterial RNAP, but that do not inhibit, or that inhibit substantially less well, an activity of eukaryotic RNAP. This differentiation is important, because it permits the identification of bacterial-RNAP-selective binding molecules and bacterial-RNAP-selective inhibitors.

The invention provides, by way of example only, a target region corresponding to, and alignable with, residues 345 and 1351 of the β' subunit and residues 1275-1292 and 1322-1326 of the β subunit of RNAP from *Escherichia coli*, as well as corresponding residues of the g' and β subunits of RNAP from *Haemophilus influenzae, Vibrio cholerae, Pseudomonas aeruginosa, Treponema pallidum, Borrelia burgdorferi, Xyella fastidiosa, Campylobacter jejuni, Neisseria meningitidis, Rickettsia prowazekii, Thermotoga maritima, Chlamydia trachomatis, Mycoplasma pneumoniae, Bacillus subtilis, Staphylococcus aureus, Mycobacterium tuberculosis, Synechocystis* sp., *Aquifex aeolicus, Deinococcus radiodurans, Thermus thermophilus,* and *Thermus aquaticus* (FIG. 3). This target region is the bacterial RNAP homologous switch-region amino-acid sequence.

The invention also provides compounds that bind to RNAP from a bacterial species, by making specific interactions with at least one residue within the set of residues corresponding to, and alignable with, residues 345 and 1351 of the β' subunit and residues 1275-1292 and 1322-1326 of the β subunit of RNAP from *Escherichia coli*.

The invention also provides compounds that inhibit an activity of RNAP from a bacterial species, by making specific interactions with at least one residue within the set of residues corresponding to, and alignable with, residues 345 and 1351 of the β' subunit and residues 1275-1292 and 1322-1326 of the β subunit of RNAP from *Escherichia coli*.

The invention also provides compounds that inhibit at least one of viability of a bacterium and growth of a bacterium, by making specific interactions with at least one residue within the set of residues corresponding to, and alignable with, residues 345 and 1351 of the β' subunit and residues 1275-1292 and 1322-1326 of the β subunit of RNAP from *Escherichia coli*.

The invention provides identification of a switch-region-target-dependent inhibitory compound by screening of a chemical library for a molecule that: (a) binds to RNAP from a bacterial species, and (b) does not bind, or binds less well, to a derivative of RNAP from a bacterial species that has at least one amino acid substitution, deletion, or insertion, in a bacterial RNAP homologous switch-region amino-acid sequence.

The invention also provides identification of a switch-region-target-dependent inhibitory compound by screening of a chemical library for a molecule that: (a) inhibits enzymatic activity of RNAP from a bacterial species, and (b) does not inhibit enzymatic activity, or inhibits enzymatic activity less well, of a derivative of RNAP from a bacterial species that has at least one amino acid substitution, deletion, or insertion, in a bacterial RNAP homologous switch-region amino-acid sequence.

The invention also provides identification of a switch-region-target-dependent inhibitory compound by screening a chemical library for a molecule that: (a) inhibits DNA binding by RNAP from a bacterial species, and (b) does not inhibit DNA binding, or inhibits DNA binding less well, by a derivative of RNAP from a bacterial species that has at least one amino acid substitution, deletion, or insertion, in a bacterial RNAP homologous switch-region amino-acid sequence.

The invention also provides identification of a switch-region-target-dependent inhibitory compound by screening a chemical library for a molecule that: (a) inhibits viability or growth of a bacterium, and (b) does not inhibit viability or growth, or inhibits viability or growth less well, of a bacterium that contains a derivative of RNAP from a bacterial species that has at least one amino acid substitution, deletion, or insertion, in a bacterial RNAP homologous switch-region amino-acid sequence.

The invention also provides identification of a switch-region-target-dependent inhibitory compound by screening of a chemical library for a first molecule that competes with a second molecule for binding to RNAP from a bacterial species, said second molecule having the ability to bind to a bacterial RNAP homologous switch-region amino-acid sequence and containing a detectable group.

The invention also provides identification of a switch-region-target-dependent inhibitory compound by use of at least one of computational docking and energy calculations with a portion of the three-dimensional structure of a RNAP from a bacterial species, said portion containing at least one residue of a bacterial RNAP homologous switch-region amino-acid sequence.

The invention also provides for use of a molecule specific for a bacterial RNAP homologous switch-region amino-acid sequence to identify, isolate, and/or immobilize RNAP from a bacterial species.

The invention also provides for use of a molecule specific for a bacterial RNAP homologous switch-region amino-acid sequence to control bacterial gene expression.

The invention also provides for use of a molecule specific for a bacterial RNAP homologous switch-region amino-acid sequence to control bacterial viability or bacterial growth.

The invention also provides for use of a molecule specific for a bacterial RNAP homologous switch-region amino-acid sequence as an antibacterial agent.

One preferred aspect of the invention provides for a molecule specific for a bacterial RNAP homologous switch-region amino-acid sequence that binds to RNAP from a bacterial species, but does not bind, or binds less well, to RNAP from a mammalian species.

Another preferred aspect of the invention provides for a molecule specific for a bacterial RNAP homologous switch-region amino-acid sequence that inhibits biochemical activity of RNAP from a bacterial species, but does not inhibit biochemical activity, or inhibits biochemical activity less well, of RNAP from a mammalian species.

Another preferred aspect of the invention provides for a molecule specific for a bacterial RNAP homologous switch-region amino-acid sequence that inhibits viability or growth of a bacterial species, but does not inhibit viability or growth, or inhibits viability or growth less well, of a mammalian species.

Another preferred aspect of the invention provides for a molecule specific for a bacterial RNAP homologous switch-region amino-acid sequence that binds to and/or inhibits RNAP from a broad spectrum of bacterial species.

Another preferred aspect of the invention provides for a molecule specific for a bacterial RNAP homologous switch-region amino-acid sequence that binds to and/or inhibits RNAP from a broad spectrum of Gram-negative bacterial species.

Another preferred aspect of the invention provides for a molecule specific for a bacterial RNAP homologous switch-region amino-acid sequence that binds to and/or inhibits RNAP from a broad spectrum of Gram-positive bacterial species.

Another preferred aspect of the invention provides for a molecule specific for a bacterial RNAP homologous switch-region amino-acid sequence that binds to and/or inhibits RNAP from a broad spectrum of both Gram-negative and Gram-positive bacterial species.

Another preferred aspect of the invention provides for a molecule that binds to and/or inhibits RNAP from *Escherichia coli*, making specific interactions with at least one residue within the set consisting of residues 345 and 1351 of the β' subunit and residues 1275-1292 and 1322-1326 of the β subunit of RNAP from *Escherichia coli*.

Another preferred aspect of the invention provides for a molecule that binds to and/or inhibits RNAP from *Bacillus subtilis*, making specific interactions with at least one residue within the set consisting of residues 334 and 1165 of the β' subunit and residues 1080-1097 and 1127-1131 of the β subunit of RNAP from *Bacillus subtilis*.

The present invention further relates to a method for identifying molecules that bind to bacterial RNAP in a switch-region-target-dependent fashion. In one embodiment, *Escherichia coli* RNAP, or a fragment thereof, containing the switch-region target, is used as the test protein to assess binding, and a derivative of said RNAP or RNAP fragment having at least one of a substitution, an insertion, and a deletion within the switch-region target is used as the control protein to assess switch-region-target-dependence of binding. "Hits" optionally may be analyzed for binding to, and inhibition of, Gram-negative-bacterial RNAP, Gram-positive-bacterial RNAP, and eukaryotic RNAP I, RNAP III and RNAP III, in vivo and in vitro. "Hits" optionally may also be characterized structurally by x-ray diffraction analysis of co-crystals with RNAP or an RNAP fragment containing the switch-region target.

The present invention further relates to a method for identifying molecules that inhibit an activity of a bacterial RNAP in a switch-region-target-dependent fashion. In one embodiment, *Escherichia coli* RNAP, or a fragment thereof, containing the switch-region target, is used as the test protein to assess inhibition, and a derivative of said RNAP or RNAP fragment having at least one of a substitution, an insertion, and a deletion within the switch-region target is used as the control protein to assess switch-region-target-dependence of inhibition. "Hits" optionally may be analyzed for binding to, and inhibition of, Gram-negative-bacterial RNAP, Gram-positive-bacterial RNAP, and eukaryotic RNAP I, RNAP III and RNAP III, in vivo and in vitro. "Hits" optionally may also be characterized structurally by x-ray diffraction analysis of co-crystals with RNAP or an RNAP fragment containing the switch-region target.

The present invention further relates to a method for identifying molecules that inhibit viability and/or growth of a bacterium in a switch-region-target-dependent fashion. In one embodiment, *Escherichia coli* (preferably a to/C or tolC rfa strain of *Escherichia coli*; see Fralick, et al. (1994) *J. Bacteriol.* 176, 6404-6406) is used as the test bacterium to assess inhibition, and a derivative of *Escherichia coli* (preferably a tolC or tolC rfa strain of *Escherichia coli*; see Fralick, et al. (1994) *J. Bacteria* 176, 6404-6406) that contains an RNAP derivative having at least one of a substitution, an insertion, and a deletion within the switch-region target is used as the control to assess switch-region-target-dependence of inhibition. "Hits" optionally may be analyzed for binding to, and inhibition of, Gram-negative-bacterial RNAP, Gram-positive-bacterial RNAP, and eukaryotic RNAP I, RNAP III and RNAP III, in vivo and in vitro. "Hits" optionally may also be characterized structurally by x-ray diffraction analysis of co-crystals with RNAP or an RNAP fragment containing the switch-region target.

The invention provides at least five assay methods for identification of switch-region-target-dependent inhibitors: a) screening based on binding of a compound to the switch-region target of a bacterial RNAP or a fragment thereof; b) screening based on inhibition of an activity associated with the switch-region target of a bacterial RNAP or a fragment thereof; c) screening based on inhibition of bacterial viability and/or growth dependent on the switch-region target of a bacterial RNAP or a fragment thereof; d) screening based on competition with a second compound for binding to the switch-region target of a bacterial RNAP or a fragment thereof, said second compound having the ability to bind to the switch-region target and containing a detectable group; and e) computational screening using the three-dimensional structure of the switch-region target of a bacterial RNAP or a fragment thereof.

One of the embodiments of the present invention is an assay system designed to identify compounds that bind a bacterial RNAP, or a fragment thereof, in a manner that requires the switch-region target. The assay measures the binding of a compound to a determinant that includes at least one amino acid residue contained within a set of amino acid residues identifiable by sequence alignment and/or structure alignment as corresponding to, and alignable with, residues 345 and 1351 of the β' subunit and residues 1275-1292 and 1322-1326 of the β subunit of RNAP from *Escherichia coli*.

One of the embodiments of the present invention is an assay system designed to identify compounds that inhibit an activity of a bacterial RNAP, or a fragment thereof, in a manner that requires the switch-region target. The assay measures the inhibition of an activity, said inhibition involving the binding of a compound to a determinant that includes at least one amino acid residue contained within a set of amino acid residues identifiable by sequence alignment and/or structure alignment as corresponding to, and alignable with, residues 345 and 1351 of the β' subunit and residues 1275-1292 and 1322-1326 of the β subunit of RNAP from *Escherichia coli*.

One of the embodiments of the present invention is an assay system designed to identify compounds that inhibit viability and/or growth of a bacterium in a manner that requires the switch-region target. The assay measures the inhibition of viability and/or growth of a bacterium, said inhibition involving the binding of a compound to a determinant that includes at least one amino acid residue contained within a set of amino acid residues identifiable by sequence alignment and/or structure alignment as corresponding to, and alignable with, residues 345 and 1351 of the 3' subunit and residues 1275-1292 and 1322-1326 of the β subunit of RNAP from *Escherichia coli*.

Isolation of RNAP:

The bacterial RNAP, or bacterial RNAP derivative, can be isolated from bacteria, produced by recombinant methods, or produced through in vitro protein synthesis. Various compounds can be introduced to determine whether a tested compound binds to, inhibits an activity of, or displaces a detectable-group-containing molecule from, the bacterial RNAP or RNAP derivative in a switch-region-target-dependent manner.

Assays can be performed in vitro or in vivo, and do not necessarily require isolation of bacterial RNAP or bacterial RNAP derivative.

Test compounds can include peptides. Test compounds alternatively, or in addition, can include non-peptide chemical compounds.

Test compounds can be chosen from chemical libraries. Test compounds alternatively, or in addition, can be chosen based on information regarding the three-dimensional structure of the switch-region target, using a computational approach, such as structure-based screening or structure-based design.

Preferred strategies for identifying inhibitors include, but are not limited to: 1) affinity-selection of phage-displayed peptide libraries, 2) iterative deconvolution of solution-phase peptide libraries; 3) direct screening of solution-phase compound libraries; 4) structure-based screening; and 5) structure-based design. One of *Escherichia coli* RNAP and *Bacillus subtilis* RNAP is the preferred test protein to assess binding or inhibition of activity; one of a derivative of *Escherichia coli* RNAP having at least one substitution in the switch-region target and a derivative of *Bacillus subtilis* RNAP having at least one substitution in the switch-region target is the preferred control protein to assess switch-region-target dependence of binding or inhibition of activity. One of *Escherichia coli* (preferably a tolC or tolC rfa strain of *Escherichia coli*; see Fralick, et al. (1994) *J. Bacteriol.* 176, 6404-6406) and *Bacillus subtilis* is the preferred test bacterium to assess inhibition of viability and/or growth; one of a derivative of *Escherichia coli* (preferably a derivative of a to/C or tolC rfa strain of *Escherichia coli*; see Fralick, et al. (1994) *J. Bacteriol.* 176, 6404-6406) that contains a derivative of RNAP having at least one substitution in the switch-region target and a derivative of *Bacillus subtilis* that contains a derivative of RNAP having at least one substitution in the switch-region target is the preferred control bacterium to assess switch-region-target dependence of inhibition of viability and/or growth.

Phage-Display Approach:

Millions to billions of short peptides readily can be surveyed for tight binding to a protein target of interest by use of a phage-displayed peptide library (*Science* 249:386; (1990) *Science* 249:404; and (1990) *Proc. Natl. Acad. Sci.* 87:6378). A phage-displayed peptide library comprises a mixture of filamentous phage clones, each displaying one specific peptide sequence on the phage virion and each containing a corresponding nucleic-acid coding sequence in the phage virion. The survey is accomplished by: (1) using the protein target of interest, typically immobilized on a surface or matrix, to affinity-purify those phage that display tight-binding peptides; and (2) determining nucleic-acid sequences of affinity-purified phage, thereby determining encoded amino-acid sequences of tight-binding peptides. The survey typically employs multiple successive cycles of affinity purification (with propagation of affinity-purified phage in a suitable bacterial host between successive cycles) in order to ensure stringent affinity-purification.

To identify peptides that bind to the switch-region target, a phage-displayed peptide library can be screened in two stages: a "positive-selection" stage and a "negative-selection" stage. In the positive-selection stage, a bacterial RNAP or RNAP fragment, preferably immobilized on a surface or matrix, is used in at least one cycle of affinity-purification, collecting bound phage, in order to isolate those phage that display peptides that bind tightly to any potential target within the bacterial RNAP or RNAP fragment. In the negative-selection stage, a derivative of a bacterial RNAP or RNAP fragment having a substitution, insertion, or deletion within the switch-region target, preferably immobilized on a surface or matrix, is used in at least one cycle of affinity-purification, collecting unbound phage, in order to eliminate those phage that bind tightly to any potential targets other than the switch-region target within the bacterial RNAP or RNAP fragment.

Iterative-Deconvolution and Positional-Scanning Approaches:

Iterative deconvolution (Houghten, et al. (1991) *Nature* 354, 84-86; Ostresh, et al. (2003) *Meths. Enzymol.* 267, 220-234; Hoesl, et al. (2003) *Meths. Enzymol.* 369, 496-517) and positional scanning (Ostresh, et al. (2003) *Meths. Enzymol.* 267, 220-234; Hoesl, et al. (2003) *Meths. Enzymol.* 369, 496-517) of solution-phase peptide libraries have been established to be effective approaches to identify reaction-step-specific, structural-element-specific inhibitors for structure-function analysis in vitro (Puras, et al. (1995) *Proc. Natl. Acad. Sci. USA* 92, 11456-11460; Cassell, et al. (2000) *J. Mol. Biol.* 299, 1193-1202; Klemm, et al. *J. Mol. Biol.* 299, 1203-1215; Boldt, et al. (2004) *J. Biol. Chem.* 279, 3472-3483), to identify antibacterial agents effective against cell-envelope targets (Houghten, et al. (1991) Nature 354, 84-86; Blondele, et al. (1996) *Antimicrob. Agents Chemotehr.* 40, 1067-1071), and to identify antibacterial agents effective against intracellular targets (Gunderson & Segall (2005) *Mol. Microbiol.* 59, 1129-1148). Iterative deconvolution and positional scanning permit effective screening of solution-phase tetrapeptide, pentapeptide, hexapeptide, and heptapeptide libraries comprising up to, respectively, 160,000, 3,200,000, 64,000,000, and 1,280,000,000 distinct sequences of standard L-amino acids (Houghten, et al. (1991) *Nature* 354, 84-86; Ostresh, et al. (2003) *Meths. Enzymol.* 267, 220-234; Hoesl, et al. (2003) *Meths. Enzymol.* 369, 496-517). Iterative deconvolution and positional scanning also permit effective screening of solution-phase peptide libraries containing nonstandard amino acids, D-amino acids, and terminal or internal modifications (Houghten, et al. (1991) *Nature* 354, 84-86; Ostresh, et al. (2003) *Meths. Enzymol.* 267, 220-234; Hoesl, et al. (2003) *Meths. Enzymol.* 369, 496-517).

Iterative deconvolution and positional scanning approaches employ initial solution-phase peptide libraries organized into pools, each pool comprising multiple distinct peptide sequences (Houghten, et al. (1991) *Nature* 354, 84-86; Ostresh, et al. (2003) *Meths. Enzymol.* 267, 220-234; Hoesl, et al. (2003) *Meths. Enzymol.* 369, 496-517). The initial library is screened using an assay of interest, pools exhibiting activity are chosen for further analysis, and successive cycles of synthesis and screening of subdivided pools are employed in order to identify individual peptides exhibiting activity (Houghten, et al. (1991) *Nature* 354, 84-86; Ostresh, et al. (2003) *Meths. Enzymol.* 267, 220-234; Hoesl, et al. (2003) *Meths. Enzymol.* 369, 496-517).

To identify peptides that bind to the switch-region target, iterative deconvolution or positional scanning of a solution-phase tetrapeptide, pentapeptide, hexapeptide, and heptapeptide hexapeptide or heptapeptide library can be performed. In a preferred embodiment, iterative deconvolution or positional scanning of a solution-phase pentapeptide, hexapeptide, or heptapeptide library is performed. (There is an approximate agreement between: (a) molecular dimensions of pentapeptides, hexapeptides, and heptapeptides; and (b) molecular dimensions of the switch-region-target ligands disclosed herein, Myx, Cor, and Rip.) Requisite screening steps can be performed using any one or more of the assays described below for switch-region-target-dependent binding, switch-region-target-dependent inhibition of activity, or switch-region-target-dependent inhibition of bacterial viability or growth. In a preferred embodiment, requisite screening steps are performed using a high-throughput assay for switch-region-target-dependent inhibition of activity (see, e.g., Example 4).

Direct Screening Approach:

Chemical libraries containing up to hundreds of thousands of single compounds can be directly screened, compound by compound, for binding to a protein of interest, for inhibition of an activity of a protein of interest, and/or for inhibition of viability or growth of a bacterium. In a preferred embodiment, high-throughput screening is performed, using any one or more of the assays described below for switch-region-target-dependent binding, switch-region-target-dependent inhibition of activity, or switch-region-target-dependent inhibition of bacterial viability or growth. In an especially preferred embodiment, high-throughput screening is performed using an assay for switch-region-target-dependent inhibition of activity (see, e.g., Example 4).

High-throughput screening typically employs assays carried out in 96-, 384- or 1536-well plates, according to methods well established in the art (see, e.g., Example 4). High-throughput screening can be performed by an individual laboratory or by a dedicated high-throughput screening facility (for example, the National Screening Laboratory for the Regional Centers of Excellence for Biodefense and Emerging Infectious Disease, NSRB, which has access to over 160,000 compounds and which typically performs screens of 50,000-100,000 compounds; http:/nsrb.med.harvard.edu/).

Structure-Based-Screening Approach:

Structure-based screening permits analysis of higher numbers of compounds and higher numbers of distinct chemotypes than direct screening alone, and, as such, can permit analysis of a larger, more diverse, fraction of chemical space than direct screening alone (Muchmore & Hajduk (2003) *Curr. Opin. Drug Discov. Dev.* 6, 544-549; Alvarez, J. (2004) *Curr. Opin. Chem. Biol.* 8, 365-370; Shoichet, B. (2004) *Nature* 432, 862-865; Jorgensen, W. (2004) *Science* 303, 1813-1818). Structure-based screening typically entails two stages. In the first stage, virtual screening of a large library of compounds (e.g., 100,000-1,000,000 compounds) is performed in order to identify candidate compounds for further analysis; in this stage, for each compound, computational docking of the compound to the binding site of interest is carried out, binding free energy is estimated, and a score is assigned. In the second stage, confirmatory direct screening of a small number of highest-scoring candidate compounds (e.g., 10-100 compounds) is performed in order to validate and re-rank candidate compounds.

The first stage, entailing virtual screening, can be performed by use of virtual-screening software packages, including, but not limited to, Glide, GOLD, ICM, LigandFit, FlexX, and DOCK (see Perola, et al. (2004) *Proteins* 56, 235-249; Kellenberger, et al. (2004) *Proteins* 57, 225-242; Kontoyianni, et al. (2004) *J. Med. Chem.* 47, 558-565; Chen, et al. (2006) *J. Chem. Info Model.* 46, 401-415). In a preferred embodiment, enhancements that allow for consideration of binding-site flexibility and that thereby improve scoring accuracy, can be incorporated (see, e.g., Sherman, et al. (2006) *J. Med. Chem.* 49, 534-553). In a preferred embodiment, virtual screening employs a virtual compound library comprising structures of at least 1,000,000 purchasable compounds (e.g., the virtual; library available through Schrödinger, Inc.) and employs at least one structural template for the switch-region target, said structural template being the three-dimensional structure of the switch-region target as in a crystal structure of unliganded bacterial RNAP or the three-dimensional structure of the switch-region target as in a crystal structure of a complex of bacterial RNAP with a switch-region-target-dependent inhibitor. The use of multiple, different structural templates in parallel (e.g., the three-dimensional structure of the switch-region target as in a crystal structure of unliganded bacterial RNAP and the three-dimensional structure of the switch-region target as in a crystal structure of a complex of bacterial RNAP with a switch-region-target-dependent inhibitor) is especially preferred, since the local conformation of the switch-region target—including the dimensions, volume, shape, and chemical character of the pocket that serves the binding site for potential inhibitors—can differ for different structural templates, and, correspondingly, the universe of potential inhibitors can differ for different structural templates.

The second stage, entailing confirmatory direct screening, can be performed using any one or more of the assays described below for switch-region-target-dependent binding, switch-region-target-dependent inhibition of activity, or switch-region-target-dependent inhibition of bacterial viability or growth. In a preferred embodiment, confirmatory direct screening is performed assessing approximately 100 highest-ranked purchasable candidate compounds for each structural template, and is performed in high-throughput format using an assay for switch-region-target-dependent inhibition of activity (see, e.g., Example 4).

Structure-Based-Design Approach:

Starting with the three-dimensional structure of a switch-region target, or of a complex of a switch-region target and a switch-region-target-dependent ligand, potential ligands for the target can be examined through the use of computational modeling using a docking program, such as Glide, GOLD, ICM, LigandFit, FlexX, or DOCK (see Perola, et al. (2004) *Proteins* 56, 235-249; Kellenberger, et al. (2004) *Proteins* 57, 225-242; Kontoyianni, et al. (2004) *J. Med. Chem.* 47, 558-565; Chen, et al. (2006) *J. Chem. Info. Model.* 46, 401-415). This procedure can include computer fitting of potential ligands to the switch-region target to ascertain the degree of compatibility between the shape and the chemical structure of the potential ligand and the shape and chemical structure of the switch-region target. Computational methods also be can employed to estimate the attraction, repulsion, and steric hindrance of a potential ligand with the switch-region target.

Known ligands of the switch-region target can be systematically modified by computer modeling programs until one or more promising potential new ligands are identified. In addition, promising potential new ligands can be systematically modified by computer modeling programs until one or more next-generation promising potential new ligands are identified. This approach has been shown to be effective in the development of HIV protease inhibitors (Lam et al., *Science* 263:380-384 (1994); Wlodawer et al., *Ann. Rev. Biochem.* 62, 543-585 (1993); Appelt, (1993) *Perspectives in Drug Discovery and Design* 1, 23-48; Erickson (1993) *Perspectives in Drug Discovery and Design* 1, 109-128).

Once a potential new ligand of the switch-region target is identified, it may be obtained from libraries of chemicals as are available from most large chemical companies including Merck, Glaxo Welcome, Bristol Meyers Squibb, Monsanto, Novartis, and Pfizer, or, alternatively, it may be synthesized. The synthesis of one compound, or even a group of compounds, is reasonable in the art of drug design. The potential new ligand then may be subjected to confirmatory direct screening, performed using any one or more of the assays described below for switch-region-target-dependent binding, switch-region-target-dependent inhibition of activity, or switch-region-target-dependent inhibition of bacterial viability or growth.

When a new ligand of the switch-region-target is identified—by a structure-based design approach or by any of the above-described approaches—a crystal can be obtained of a complex of a bacterial RNAP or RNAP fragment and the new ligand, either by soaking or by de novo crystallization, and a crystal structure can be determined of said complex. Preferably, the crystal can effectively diffract x-rays for the determination of the atomic coordinates of said complex to a resolution of better than 4.0 Å. The crystal structure can be determined by molecular replacement. Molecular replacement involves using a known three-dimensional structure, in this case the three-dimensional structure of unliganded bacterial RNAP or RNAP fragment, as a search model to determine the structure of a closely related molecule or protein-ligand complex in a new crystal form. The measured x-ray diffraction properties of the new crystal are compared with the search model structure to compute the position and orientation of the protein in the new crystal. Computer programs that can be used include: X-PLOR, CNS, (Crystallography and NMR System, a next level of XPLOR), and AMORE (J. Navaza, *Acta Crystallographics ASO,* 157-163 (1994)). Once the position and orientation are known, an electron density map can be calculated using the search model to provide X-ray phases. Thereafter, the electron density can be inspected for structural differences and the search model can be modified to conform to the new structure.

Assay Components:

The bacterial RNAP, or RNAP fragment or derivative, containing the switch-region target, and an inhibitory compound specific to the switch region of RNAP, which are binding partners used as components in the assay, may be derived from natural sources (e.g., purified from bacterial RNAP using protein separation techniques well known in the art); produced by recombinant DNA technology using techniques known in the art (see, e.g., Sambrook et al., 1989, Molecular Cloning: A Laboratory Manual, Cold Spring Harbor Laboratories Press, Cold Spring Harbor, N.Y.); and/or chemically synthesized in whole or in part using techniques known in the art (see, e.g., Creighton, 1983, Proteins: Structures and Molecular Principles, W. H. Freeman & Co., N.Y., pp. 50-60).

Where recombinant DNA technology is used to produce the bacterial RNAP, RNAP fragment, or derivative containing the switch-region target, it may be advantageous to engineer fusion proteins that can facilitate labeling, immobilization and/or detection. For example, the coding sequence of a bacterial RNAP switch region can be fused to that of a heterologous protein that has enzyme activity or serves as an enzyme substrate in order to facilitate labeling and detection. The fusion constructs should be designed so that the heterologous component of the fusion product does not interfere with binding of the bacterial RNAP switch region and an inhibitory compound specific to the switch region of RNAP.

For a binding assay, one of the binding partners used in the assay system may be labeled, either directly or indirectly, to facilitate detection of a complex formed between the bacterial RNAP switch region and an inhibitory compound specific to the switch-region target of RNAP. Any of a variety of suitable labeling systems may be used including, but not limited to, radioisotopes such as $^{125}$I; enzyme labeling systems that generate a detectable colorimetric signal or light when exposed to substrate; and fluorescent labels.

Fluorescent labels are preferred.

Indirect labeling involves the use of a third protein, such as a labeled antibody, which specifically binds to an entity containing a switch-region target. Such antibodies include, but are not limited to, polyclonal, monoclonal, chimeric, humanized, single chain, Fab fragments and fragments produced by an Fab expression library.

For the production of antibodies, various host animals may be immunized by injection with at least one segment of an entity containing a switch-region target. Such host animals may include, but are not limited to, rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique that provides for the production of antibody molecules by continuous cell lines in culture. These include, but are not limited to, the hybridoma technique originally described by Kohler and Milstein, (1975) *Nature* 256:495-497), the human B-cell hybridoma technique (Kosbor et al. (1983) *Immunology Today*, 4:72, Cote et al. (1983) *Proc. Natl. Acad. Sci.*, 80:2026-2030) and the EBV-hybridoma technique (Cole et al., 1985, Monoclonal Antibodies and Cancer Therapy, Alan R. Liss, Inc., pp. 77-96). In addition, techniques developed for the production of "chimeric antibodies" (Morrison et al. (1984) *Proc. Natl. Acad. Sci.*, 81:6851-6855; Neuberger et al. (1984) *Nature*, 312:604-608; Takeda et al. (1985) *Nature*, 314:452-454) by splicing the genes from a mouse antibody molecule of appropriate antigen specificity together with genes from a human antibody molecule of appropriate biological activity. Alternatively, techniques described for the production of single-chain antibodies (e.g., U.S. Pat. No. 4,946,778) can be adapted to produce single-chain antibodies specific to an entity containing a switch-region target.

Antibody fragments that recognize specific epitopes may be generated by known techniques. For example, such fragments include, but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al. (1989) *Science*, 246:1275-1281) to allow rapid and easy identification of monoclonal Fab fragments with the desired specificity.

Binding Assays:

Binding assays can be conducted in a heterogeneous or homogeneous format. A heterogeneous assay is an assay in which reaction results are monitored by separating and detecting at least one component during or following reaction. A homogeneous assay is an assay in which reaction results are monitored without separation of components.

In either approach, the order of addition of reactants can be varied to obtain different information about the compounds being tested.

In one example of a heterogeneous binding assay system, one binding partner—e.g., either an entity containing a switch-region target or a compound specific to the switch-region target—is anchored onto a solid surface, and the other binding partner, which is not anchored, is labeled, either directly or indirectly. In practice, microtiter plates are conveniently utilized. The anchored species may be immobilized by non-covalent or covalent attachments. Alternatively, an immobilized antibody specific for the an entity containing a switch-region target may be used to anchor the entity to the solid surface. The surfaces may be prepared in advance and stored. In order to conduct the assay, the non-immobilized binding partner is added to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

In a preferred embodiment of the invention, a homogeneous binding assay is used. In one preferred embodiment of the invention, involving use of a homogeneous binding assay, a preformed complex of an entity containing a switch-region target and a compound that binds to the switch-region target is prepared, in which at least one of the binding partners contains a detectable group having that exhibits a difference in a detectable property in the complex state and in the free state (see, e.g., U.S. Pat. No. 4,109,496); the addition of a test compound that competes with, and displaces, one of the binding partners from the preformed complex results in a change in a detectable properties of the detectable group, permitting identification of test substances able to bind to the switch-region target.

One aspect of the invention provides fluorescence resonance energy transfer (FRET)-based homogeneous assays (Förster (1948) Ann. Physik. (Leipzig) 2, 55-75; reviewed in Lilley and Wilson (2000) Curr. Opin. Chem. Biol. 4, 507-517; Selvin, P (2000) *Nature Structl. Biol.* 7, 730-734; Mukhopadhyay et al., 2001 *Cell* 106, 453-463; Mekler, et al. (2002) *Cell* 108, 599-614; Mukhopadhyay, et al. (2004) *Mol. Cell.* 14, 739-751). FRET occurs in a system having a first fluorescent probe serving as a donor and a second fluorescent probe or chhomophore serving as an acceptor, where the emission wavelength of the donor overlaps the excitation wavelength of the acceptor. In such a system, upon excitation of the donor with light of its excitation wavelength, energy can be transferred from the donor to the acceptor, resulting in excitation of the acceptor and omission at the acceptor's emission wavelength. With commonly used fluorescent probes, FRET permits accurate determination of distances in the range of ~20 to ~100 Å. FRET permits accurate determination of distances up to more than one-half the diameter of a transcription complex (diameter ~150 Å; see Zhang et al. 1999; Cramer et al. (2001) *Science* 292, 1863-1876; Gnatt et al. (2001) *Science* 292, 1876-1882).

A preferred assay involves monitoring of FRET between: a) one of a fluorescent probe or a chromophore present in a bacterial RNAP, and b) one of a fluorescent probe or a chromophore present in a small molecule that binds to the switch-region target.

An especially preferred assay involves monitoring of FRET between: a) one of a fluorescent probe or a chromophore present in a bacterial RNAP, and b) one of a fluorescent probe or a chromophore present in one of Myx, Cor, or Rip (see, e.g., Example 1, section 1c).

Activity Assays:

In a particular embodiment, the effect of a test compound on an activity of a bacterial RNAP, or a fragment thereof, is determined (either independently of, or subsequent to, a binding assay as exemplified above). In one such embodiment, the extent or rate of the DNA-dependent RNA synthesis is determined. For such assays, a labeled nucleotide can be used. The assay can include the withdrawal of aliquots from the incubation mixture at defined intervals and subsequent analysis. Alternatively, the assay can be performed using a real-time assay (e.g., with a fluorescently labeled nucleotide or with a fluorescent probe for RNA).

One assay for RNAP activity is a modification of the method of Burgess et al. (*J. Biol. Chem.*, 244:6160 (1969); see http://www.worthington-biochem.com/manual/R/RNAP.html). One unit incorporates one nanomole of UMP into acid insoluble products in 10 minutes at 37° C. under the assay conditions such as those listed below. The suggested assay conditions are: (a) 0.04 M Tris-HCl, pH 7.9, containing 0.01 M $MgCl_2$, 0.15 M KCl, and 0.5 mg/ml BSA; (b) nucleoside triphosphates (NTP): 0.15 mM each of ATP, CTP, GTP, UTP; spiked with $^3$H-UTP 75000-150000 cpms/0.1 ml; (c) 0.15 mg/ml calf thymus DNA; (d) 10% cold perchloric acid; and (e) 1% cold perchloric acid. A starting enzyme concentration of 0.1-0.5 units of RNAP in 5 μl-10 μl are used as the starting enzyme concentration.

The procedure is to add 0.1 ml Tris-HCl, 0.1 ml NTP and 0.1 ml DNA to a test tube for each sample or blank. At time zero, enzyme (or buffer for blank) is added to each test tube, and the contents are then mixed and incubated at 37° C. for 10 minutes. 1 ml of 10% perchloric acid is added to the tubes to stop the reaction. The acid insoluble products can be collected by vacuum filtration through Millipore filter discs having a pore size of 0.45 u-10 u (or equivalent). The filters are then washed four times with 1% cold perchloric acid using 1 ml-3 ml for each wash. These filters are then placed in scintillation vials. Two ml of methyl cellosolve are added to the scintillation vials to dissolve the filters. When the filters are completely dissolved (after about five minutes) 10 ml of scintillation fluid are added and the vials are counted in a scintillation counter.

Additional assays for analysis of RNAP activity contemplated by the present invention include fluorescence-detected abortive initiation assays, fluorescence-detected transcription assays, and molecular-beacon-based transcription assays. An especially preferred assay is the fluorescence-detected abortive initiation assay (see Example 4).

In assays of RNAP activity, different orders of addition of components may be employed. In preferred embodiments, an order of addition is employed in which RNAP or RNAP derivative is pre-incubated with the test compound—affording time and opportunity for formation of a complex between RNAP or RNAP derivative and the test compound—before RNAP is incubated with DNA.

Antibacterial Assays:

Methods of testing a compound for antibacterial activity in cultures are well known in the art, and can include standard assays of minimum inhibitory concentration (MIC; see, e.g., Examples 1-3, Tables 1 and 2-6) and of minimum bacteriocidal concentration (MBC).

Animal Model Assays:

Inhibitors of bacterial RNAP identified by the processes of the present invention can be assayed in animal experiments. The ability of an inhibitor to control bacterial infection can be assayed in animal models that are natural hosts for the bacterial species of interest. Such animal models may involve mammals, such as rodents, dogs, pigs, horses, and primates. Such animal models can be used to determine the $LD_{50}$ and the $ED_{50}$ in animal subjects, and such data can be used to derive the therapeutic index for the inhibitor. In animal models, test compounds can be administered by a variety of routes including topical, oral, subcutaneous, and intraperitoneal routes, depending on the proposed use. Generally, at least two groups of animals are used in the assay, with at least one group being a control group, which is administered the administration vehicle without the test compound.

Pharmaceutical Preparations and Methods of Administration:

Identified compounds that inhibit bacterial replication can be administered to a patient at therapeutically effective doses to treat bacterial infection. A therapeutically effective dose refers to that amount of the compound sufficient to result in amelioration of symptoms of bacterial infection.

Toxicity and therapeutic efficacy of such compounds can be determined by standard pharmaceutical procedures in cell cultures or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of infection in order to minimize damage to uninfected cells and reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal infection, or a half-maximal inhibition) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

DEFINITIONS

As used herein a "small molecule" is a compound that has a molecular weight of less than approximately 15 kDa.

As used herein a "small organic molecule" is an organic compound [or organic compound complexed with an inorganic compound (e.g., metal)] that has a molecular weight of less than approximately 3 kDa.

As used herein the term "about" preferably means within 10 to 15%, preferably within 5 to 10%. For example, an amino acid sequence that contains about 60 amino acid residues preferably contains between 51 to 69 amino acid residues, more preferably 57 to 63 amino acid residues.

As used'herein the term "switch-region target" comprises amino acid residues corresponding to, and alignable with, residues 345 and 1351 of the β' subunit and residues 1275-1292 and 1322-1326 of the β subunit of RNAP from *Escherichia coli*, or a set of residues corresponding to, and alignable with residues 334 and 1165 of the β' subunit and residues 1080-1097 and 1127-1131 of the β subunit of RNAP from *Bacillus subtilis* (FIGS. 2,3).

As used herein the term "homologous switch-region amino-acids sequence" comprises amino acid residues corresponding to, and alignable with, residues 345 and 1351 of the β' subunit and residues 1275-1292 and 1322-1326 of the β subunit of RNAP from *Escherichia coli*, or a set of residues corresponding to, and alignable with residues 334 and 1165 of the β' subunit and residues 1080-1097 and 1127-1131 of the β subunit of RNAP from *Bacillus subtilis* (FIGS. 2,3).

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc) (Reeck et al. (1987) *Cell* 50, 667).

Accordingly, the term "sequence similarity" in all its grammatical forms refers to the degree of identity or correspondence between nucleic acid or amino acid sequences of proteins that do not share a common evolutionary origin (see Reeck et al., 1987, supra). However, in common usage and in the instant application, the term "homologous" may refer to sequence similarity and not a common evolutionary origin.

The term "corresponding to" is used herein to refer to similar or homologous sequences, whether the exact position is identical or different from the molecule to which the similarity or homology is measured. Thus, the term "corresponding to" refers to the sequence similarity, and not the numbering of the amino acid residues or nucleotide bases.

The present invention contemplates isolation of nucleic acids encoding the target. The present invention further provides for subsequent modification of the nucleic acid to generate a fragment or modification of the target.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

EXAMPLES

Figure 4:
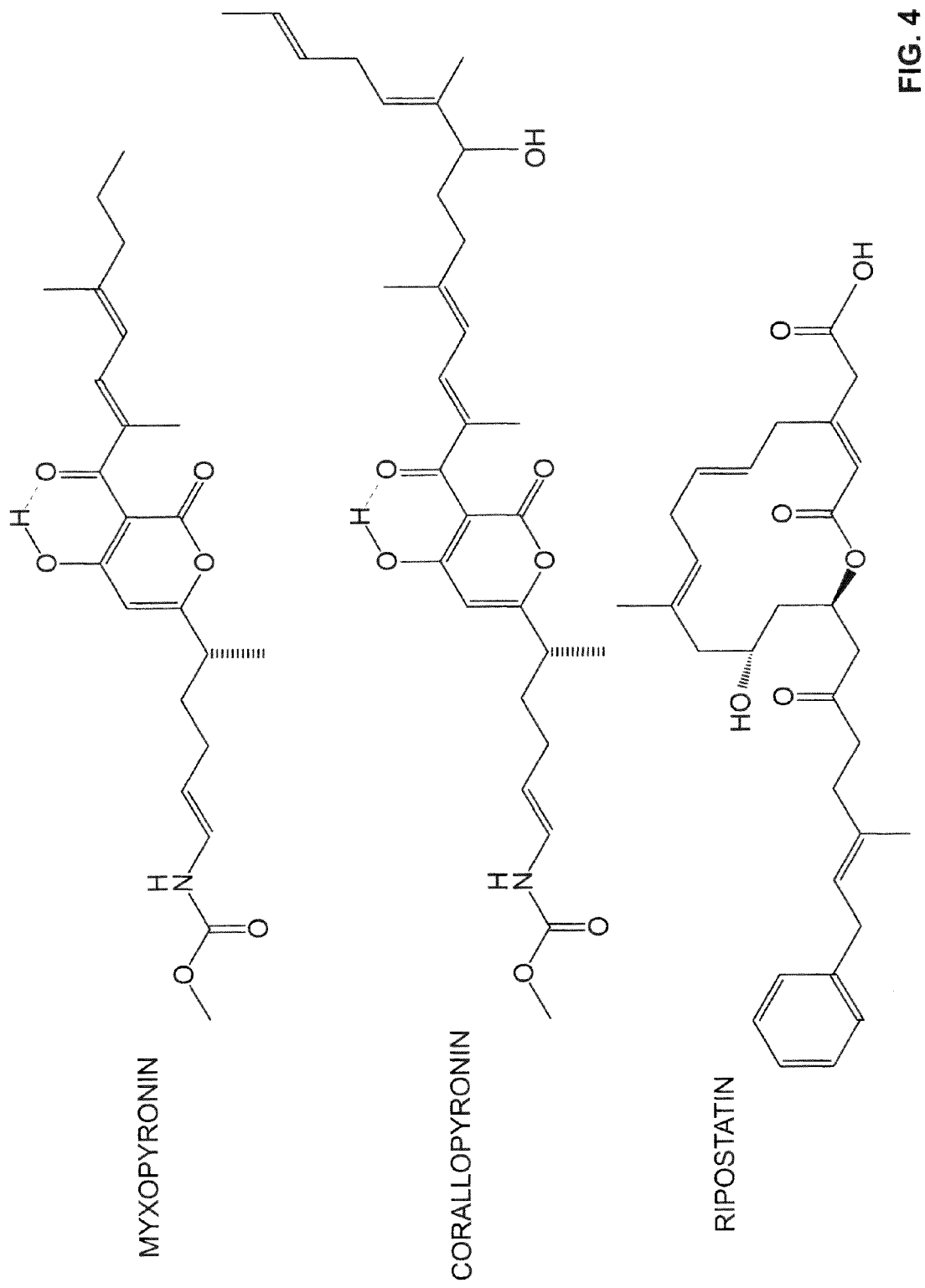
FIG. 4 shows the chemical structures of myxopyronin (Myx), corallopyronin (Cor) and ripostatin (Rip).

With reference to the examples below, Applicant has identified three compounds that inhibit bacterial RNAP through interactions with the RNAP switch region and that appear to function by preventing clamp opening required for DNA binding and/or clamp closure required for DNA retention: myxopyronin (Myx), corallopyronin (Cor), and ripostatin (Rip). The structures of these compounds are shown in FIG. 4. The three compounds interact with residues that are conserved in Gram-positive and Gram-negative bacterial RNAP, and, accordingly, exhibit broad-spectrum antibacterial activity. The three compounds interact, in part, with residues that are not conserved in eukaryotic RNAP I, RNAP II, and RNAP III, and, accordingly, do not exhibit cross-inhibition of eukaryotic RNAP. The three compounds interact with residues that are remote from the binding site for the rifamycins and from the binding sites for other characterized RNAP inhibitors, and, accordingly, do not exhibit cross-resistance with rifamycins or other characterized RNAP inhibitors. Taken together, these properties render the three compounds exceptionally attractive candidates for development as antibacterial therapeutic agents.

Example 1

Switch-Region-Target Inhibitors: MYX

The present example is directed to the use of myxopyronin (Myx) as a small-molecule inhibitor of bacterial RNAP that, based on Applicant's discovery, functions through interaction with the bacterial RNAP homologous amino-acid sequence.

Myx is a polyketide-derived α-pyrone antibiotic (Irschik, et al. (1983) *J. Antibiot* 36, 1651-1658; Kohl, et al. (1983) *Liebigs Ann. Chem.* 1656-1667; Kohl, et al. (1984) *Liebigs Ann. Chem.* 1088-1093; FIG. 4). Myx is produced by *Myxococcus fulvus* strain Mxf50 (DSM 2549; Irschik, et al. (1983) *J. Antibiot* 36, 1651-1658). The compound inhibits growth of Gram-positive and Gram-negative bacterial species, including *Bacillus subtilis, B. megaterium, Staphylococcus aureus, Micrococcus luteus, Enterococcus faecium, Enterobacter cloacae, Corynebacterium mediolanum, Mycobacterium* smegmatis, Acinetobacter calcoaceticus, Pseudomonas aeruginosa, and Escherichia coli DH21tolC (MICs≦10 μg/ml for all; MICs≦1 μg/ml for S. aureus, A. calcoaceticus, and Escherichia coli DH21tolC; Irschik, et al. (1983) Supra; Kohl, et al. (1983) Supra; unpublished data). The compound is bacteriocidal, as assessed with Escherichia coli DH21 tolC (unpublished data). The compound inhibits bacterial RNAP ($K_i$=1 μM) but does not inhibit eukaryotic RNAP II (Irschik, et al. (1983) Supra; unpublished data). The compound exhibits no acute toxicity in mice at concentrations up to 100 mg/kg (Irschik, et al. (1983) Supra). The compound exhibits no cross-resistance with rifamycins, CBR-703, or microcin J25 (Hu, et al. (1988) Supra; unpublished data). Two total syntheses of racemic Myx have been reported (Hu, et al. (1988) *J. Org. Chem.* 63, 2401-2406; Doundoulakis, et al. (2004) *Bioorg. Med. Chem. Lett.* 14, 5667-5672).

1. Myx: Target of Transcription Inhibition a. Myx Requires the Switch-Region Target: Results of Random Mutagenesis and Selection.

To identify determinants for function of Myx, Applicant has performed random mutagenesis of genes encoding *Escherichia coli* RNAP β' subunit (rpoC) and β subunit (rpoB), and has isolated and sequenced five independent Myx-resistant mutants (methods as described in Mukhopadhyay, et al. (2004) *Mol. Cell.* 14, 739-751).

Figure 5:
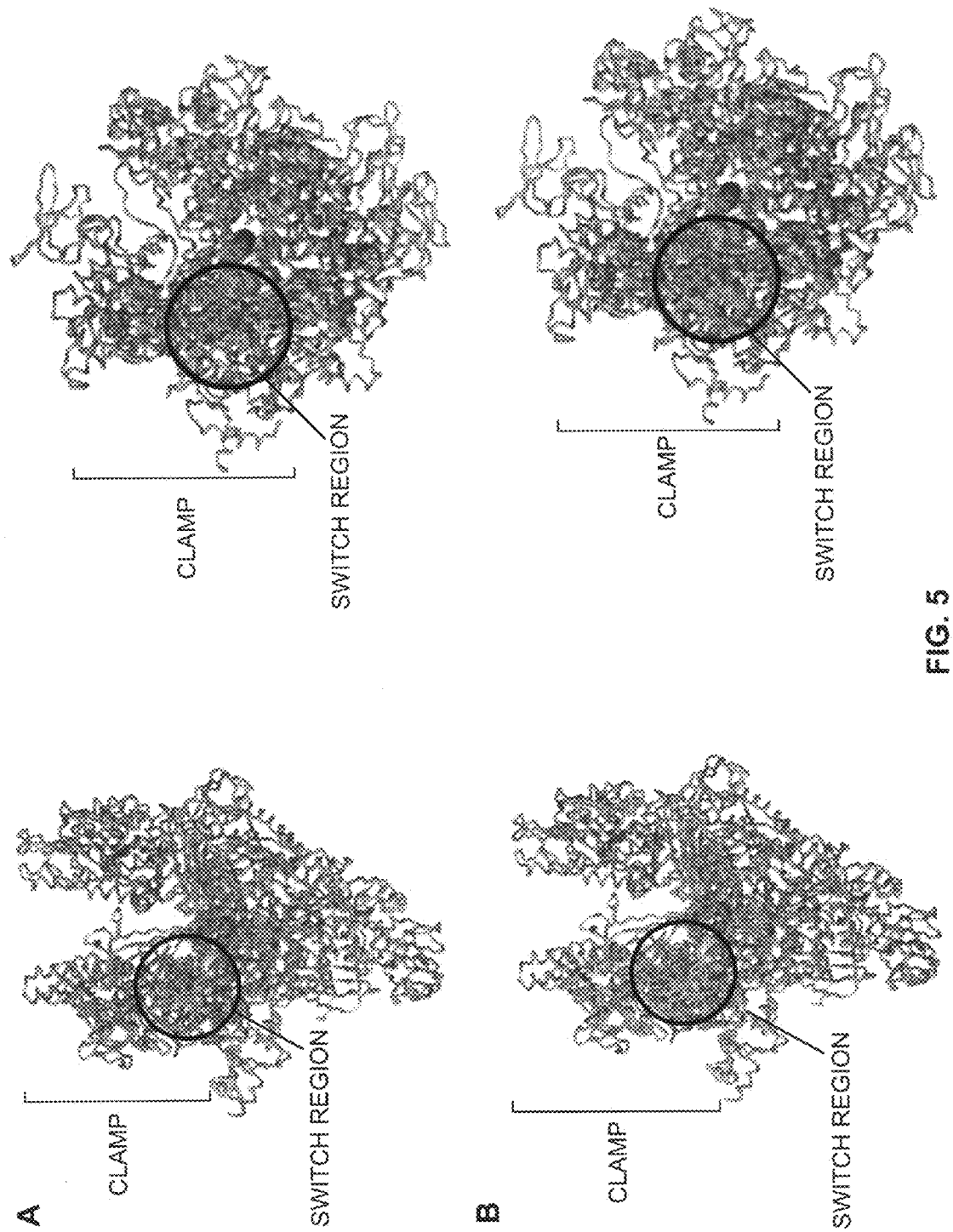
FIG. 5 shows the locations of Myx-resistant substitutions within the three-dimensional structure of bacterial RNAP (β' nonconserved domain and σ omitted for clarity). Red, sites of single-residue substitutions conferring high-level Myx-resistance; pink, sites of single-residue substitutions conferring moderate-level Myx-resistance; violet sphere, active-center $Mg^{2+}$. Two orthogonal views are shown: at left, a view through the RNAP active-center cleft; at right, a view directly into the RNAP active-center cleft. (A) Myx-resistant substitutions from random mutagenesis and selection. (B) Myx-resistant substitutions from saturation mutagenesis and selection.

Results are presented in Table 1 and FIG. 5A. Substitutions conferring Myx-resistance were obtained at β' residue 345 (three isolates) and at β residues 1275 (one isolate) and 1292 (one isolate) (Table 1). In the three-dimensional structure of bacterial RNAP, the sites of the Myx-resistant substitutions identified by random mutagenesis and selection define a discrete, continuous determinant with dimensions of approximately 10×10×5 Å (FIG. 5A). The determinant is located within the bacterial RNAP switch region and, in particular, is located within the bacterial RNAP homologous switch-region amino-acid sequence (FIG. 5A; compare FIG. 2). All substitutions conferring Myx-resistance affect residues of the bacterial RNAP homologous switch-region amino-acid sequence (compare FIG. 3). The results establish that inhibition of transcription by Myx requires the bacterial RNAP switch-region homologous amino-acid sequence.

TABLE 1

Myx$^r$ isolates from random mutagenesis and selection

| amino acid substitution | codon substitution | number of independent isolates | MIC ratio |
|---|---|---|---|
| rpoC | | | |
| 345 Lys→Asn | AAG→AAT | 2* | 32 |
| 345 Lys→Thr | AAG→ACG | 1 | 32 |
| rpoB | | | |
| 1275 Val→Met | GTG→ATG | 1** | >32 |
| 1291 Leu→Phe | CTC→TTC | 1 | 2 |

*One isolate obtained as double mutant 340 Gln→Leu; 345 Lys→Asn.
**Isolated as double mutant 857 Val→Met; 1275 Val→Met; phenotype confirmed as single mutant constructed by site-directed mutagenesis b. Myx Requires the Switch-Region Target: Results of Saturation Mutagenesis and Selection.

To further define determinants for function of Myx, Applicant has performed saturation mutagenesis of genes encoding *Escherichia coli* RNAP β' subunit (rpoC) and β subunit (rpoB), and has isolated and sequenced more than 100 independent Myx-resistant mutants (methods as described in Mukhopadhyay, et al. (2004) *Mol. Cell.* 14, 739-751; Tuske, et al. (205) *Cell* 122, 541-552). Saturation mutagenesis was performed using a set of "doped" oligodeoxyribonucleotide primers targeting all codons for residues located within 30 Å of β' residue 345 and β residues 1275 and 1292 in the three-dimensional structure of bacterial RNAP (primer sequences in Table 2).

Figure 6:
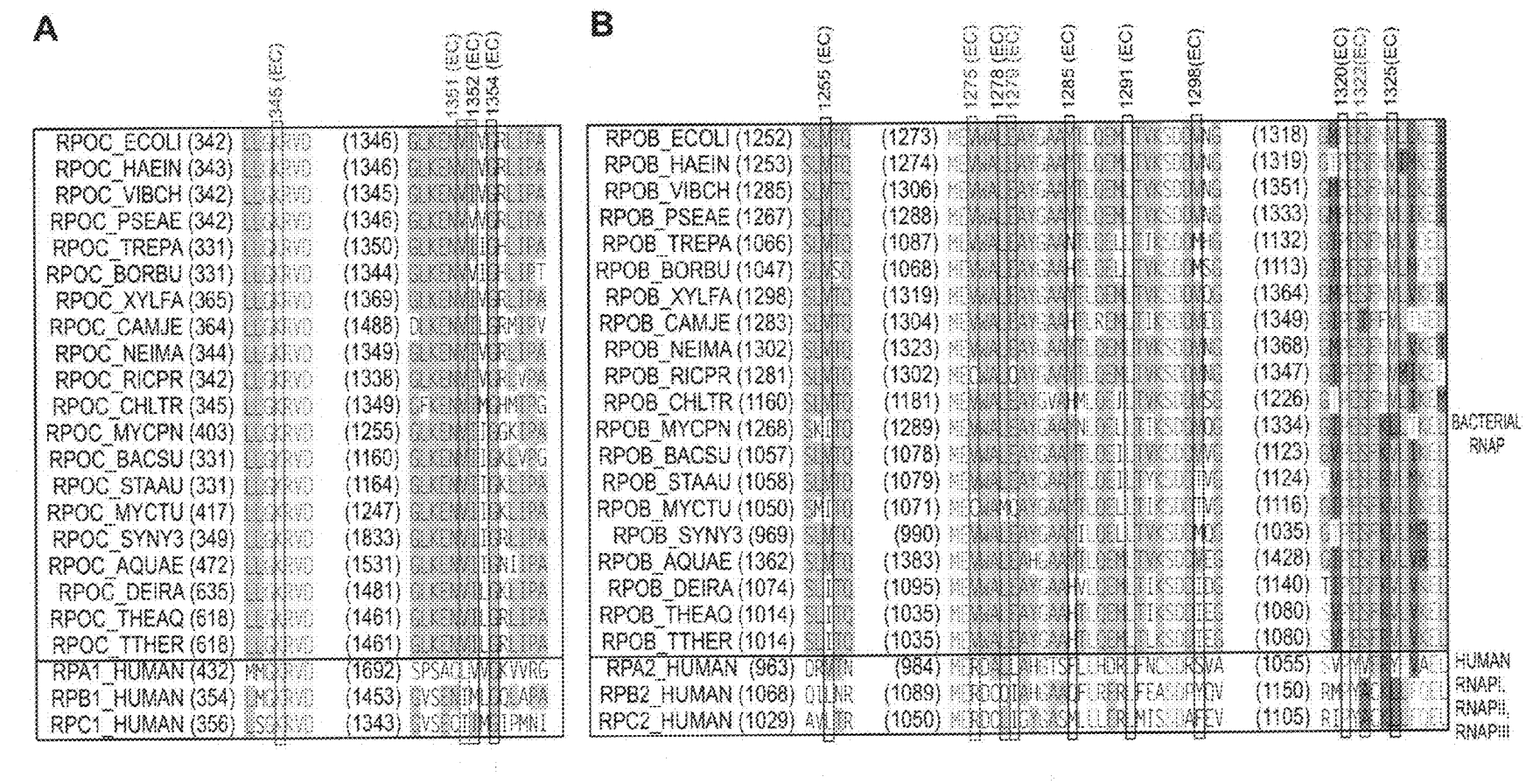

Results are presented in Table 3, FIG. 5B, and FIG. 6. Single-residue substitutions conferring Myx-resistance were obtained at β' residues 345 and 1351, and at β residues 1255, 1275, 1278, 1279, 1285, 1298, 1315, 1317, 1320, 1322, and 1325 (Table 3). In the three-dimensional structure of bacterial RNAP, the sites of the Myx-resistant substitutions define a determinant with dimensions of approximately 20×20×10 Å (FIG. 5B). The determinant is located within the bacterial RNAP switch region and, in particular, is located within the bacterial RNAP homologous switch-region amino-acid sequence (FIG. 5B; compare FIG. 2). All five high-level Myx-resistant substitutions affect residues of the bacterial RNAP homologous switch-region amino-acid sequence (β' residues 345 and 1351 and β residues 1275, 1279, and 1322; FIG. 6; compare FIG. 3). Four of five high-level Myx-resistant substitutions affect residues that are conserved in bacterial RNAP but that are not conserved in eukaryotic RNAP I, RNAP II, or RNAP III, consistent with the selectivity of Myx (β' residue 1351 and β residues 1275, 1279, and 1322; FIG. 6). The results establish that inhibition of transcription by Myx requires the bacterial RNAP switch-region homologous amino-acid sequence.

TABLE 2

"doped" oligonucleotide primers used in saturation mutagenesis

| codons targeted | sequence |
|---|---|
| rpoC | |
| 325-335 | GCGTCCTCTGAAATCTTTGGCCGACATGATCAAAGGTAAA CAGGGTCGTTTCCG (SEQ ID NO 116) |
| 336-346 | GGTAAACAGGGTCGTTTCCGTCAGAACCTGCTCGGTAAGC GTGTTGACTACTCC (SEQ ID NO 117) |
| 347-355 | CGGTAAGCGTGTTGACTACTCCGGTCGTTCTGTAATCACC GTAGGTC (SEQ ID NO 118) |
| 429-433 | TGCACCGACTCTGCACCGTCTGGGTATCCAGGCAT (SEQ ID NO 119) |
| 466-481 | GGTGACCAGATGGCTGTTCACGTACCGCTGACGCTGGAAG CCCAGCTGGAAGCGCGTGCGCTGATG (SEQ ID NO 120) |
| 794-807 | GCGAACTCCGGTTACCTGACTCGTCGTCTGGTTGACGTGG CGCAGGACCTGGTGGTTACCG (SEQ ID NO 121) |
| 913-924 | CAACAAGGGT GAAGCAATCGGTGTTATCGCGGCACAGTCC ATCGGTGAACCGGGTA (SEQ ID NO 122) |
| 1319-1327 | AACCGAGTCCTTTCATCTCCGCGGCATCGTTCCAGGAGAC CACTCGC (SEQ ID NO 123) |
| 1347-1360 | CTGCGCGG CTGAAAGAGAACGTTATCGTGGGTCGTCTGAT CCCGGCAGGTACCGGTTACGC (SEQ ID NO 124) |

TABLE 2-continued

"doped" oligonucleotide primers used
in saturation mutagenesis

| codons targeted | sequence |
|---|---|
| rpoB | |
| 1248-1256 | GCACGCGCGTTCCACCGGTTCTTACAGCCTGGTTACTCAG CAGCCGCTGG (SEQ ID NO 125) |
| 1257-1262 | GGTTACTCAGCAGCCGCTGGGTGGTAAGGCACAGTTCG (SEQ ID NO 126) |
| 1265-1274 | TAAGGCACAGTTCGGTGGTCAGCGTTTCGGGGAGATGGAA GTGTGGGCGC (SEQ ID NO 127) |
| 1277-1287 | GGAAGTGTGGGCGCTGGAAGCATACGGCGCAGCATACACC CTGCAGGAAATGC (SEQ ID NO 128) |
| 1288-1297 | ATACACCCTGCAGGAAATGCTCACCGTTAAGTCTGATGAC GTGAACGGTC (SEQ ID NO 129) |
| 1298-1310 | GTCTGATGACGTGAACGGTCGTACCAAGATGTATAAAAAC ATCGTGGACGGCAACCATC (SEQ ID NO 130) |
| 1311-1321 | CATCGTGGACGGCAACCATCAGATGGAGCCGGGCATGCCA GAATCCTTCAACG (SEQ ID NO 131) |
| 1322-1329 | CATGCCAGAATCCTTCAACGTATTGTTGAAAGAGATTCGT TCGC (SEQ ID NO 132) |

TABLE 3

Myx[r] isolates from saturation mutagenesis and selection

| amino acid substitution | number of independent isolates | MIC ratio |
|---|---|---|
| rpoC | | |
| single-substitution mutants | | |
| 345 Lys→Arg | 6 | >32 |
| 345 Lys→Asn | 24 | 32 |
| 345 Lys→Thr | 5 | 32 |
| 1351 Val→Phe | 20 | >32 |
| Multiple-substitution mutants | | |
| 345 Lys→Asn; 451 Pro→Leu | 1 | |
| 1351 Val→Phe; 1356 Leu→Pro | 5 | |
| 1351 Val→Phe; 1357 Ile→Met | 5 | |
| 1351 Val→Phe; 1359 Ala→Thr | 2 | |
| 345 Lys→Asn; 452 Leu→Pro; 453 Val→Ala | 1 | |
| 318 Gly→Ala; 345 Lys→Asn; 430 His→Pro; 467 Ala→Gly | 1 | |
| rpoB | | |
| single-substitution mutants | | |
| 1255 Thr→Ile | 1 | 2 |
| 1275 Val→Met | 15 | >32 |
| 1275 Val→Phe | 2 | >32 |
| 1278 Leu→Val | 2 | 2 |
| 1279 Glu→Lys | 20 | >32 |
| 1285 Tyr→Asp | 1 | 2 |
| 1298 Val→Leu | 1 | 4 |
| 1315 Met→Leu | 1 | 2 |
| 1317 Pro→Leu | 2 | 2 |

TABLE 3-continued

Myx[r] isolates from saturation mutagenesis and selection

| amino acid substitution | number of independent isolates | MIC ratio |
|---|---|---|
| 1320 Pro→Ala | 1 | 2 |
| 1322 Ser→Thr | 1 | 2 |
| 1322 Ser→Tyr | 1 | 2 |
| 1322 Ser→Val | 2 | 16 |
| 1325 Val→Leu | 1 | 2 |
| Multiple-substitution mutants | | |
| 1232 Met→Ile; 1275 Val→Met | 1 | |
| 1275 Val→Met; 1298 Val→Leu | 1 | |
| 1278 Leu→Val; 1279 Glu→Lys | 1 | |
| 1279 Glu→Lys; 1285 Tyr→Asp | 1 | | c. Myx Requires a Binding Determinant in the Switch-Region Target.

Figure 7:
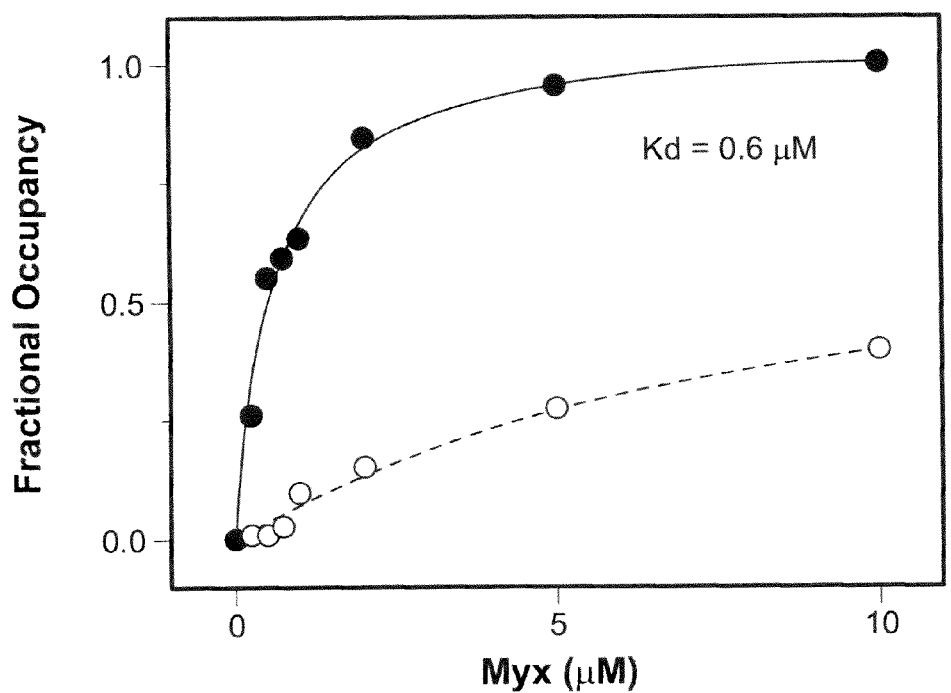
FIG. 7 presents results indicating that Myx binds to *Escherichia coli* RNAP in a switch-region-target-dependent fashion (fluorescence quenching equilibrium binding experiments; methods essentially as described in Yarbrough, et al. (1976) *J. Biol. Chem.* 15, 2669-2676). ●, wild-type RNAP; ○, [Arg 345]β'-RNAP (RNAP derivative with single-residue substitution in bacterial RNAP homologous switch-region amino acid sequence).

Applicant has performed equilibrium binding experiments with wild-type *Escherichia coli* RNAP and with [Arg345]β'-RNAP, an RNAP derivative having a single-residue substitution within the bacterial RNAP homologous switch-region amino-acid sequence (detecting binding of Myx to RNAP by monitoring quenching by Myx of fluorescence emission of RNAP Trp residues; methods analogous to those described in Yarbrough, et al. (1976) *J. Biol. Chem.* 15, 2669-2676). The results in FIG. 7 show that substitution within the bacterial RNAP homologous switch-region amino-acid sequence reduces binding of Myx, indicating that the bacterial RNAP homologous switch-region amino-acid sequence constitutes a binding determinant for Myx (as opposed to a conformational determinant required for function of Myx but not for binding of Myx).

2. Myx: Mechanism of Transcription Inhibition a. Myx Prevents Stable Interaction with Promoter DNA.

Figure 8:
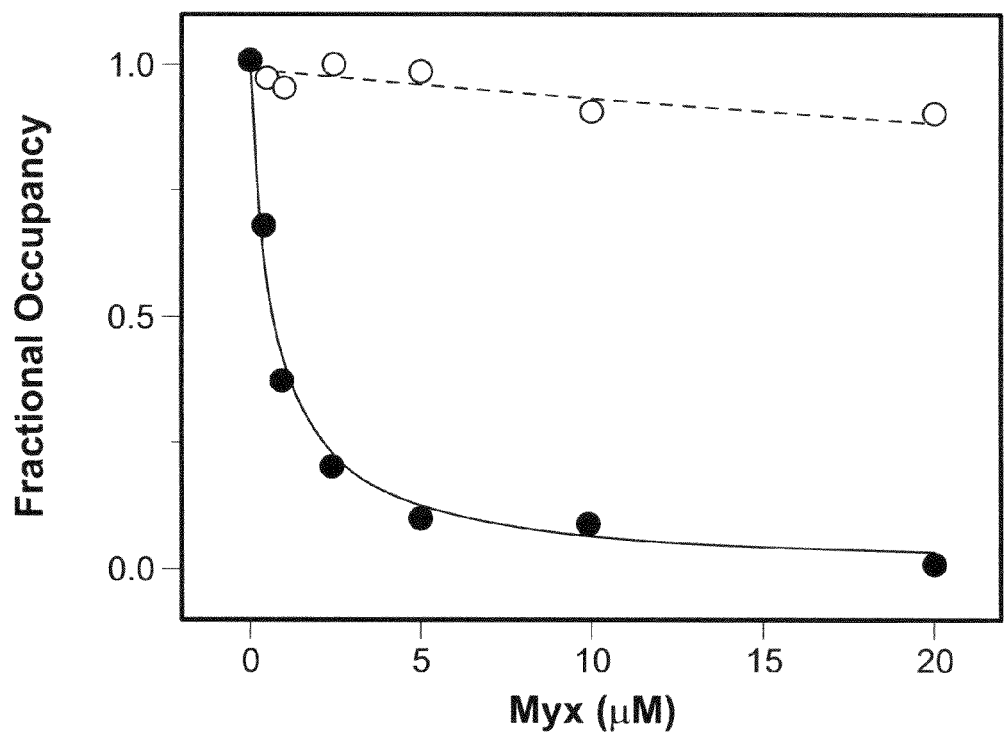
FIG. 8 presents results indicating that Myx inhibits interaction of *Escherichia coli* RNAP with promoter DNA in a switch-region-target-dependent fashion (florescence-detected electrophoretic mobility shift assays; methods as in Mukhopadhyay, et al. (2004) *Mol. Cell.* 14, 739-751). ●, wild-type RNAP; ○, [Arg 345]β'-RNAP (RNAP derivative with single-residue substitution in switch-region target). (A) DNA construct SEQ ID NO:133. (B) Data.

Applicant has performed transcription and DNA-binding experiments in order to define the basic mechanism of transcription inhibition by Myx (methods as in Mukhopadhyay, et al. (2004) *Mol. Cell.* 14, 739-751). The results indicate that Myx inhibits transcription by preventing stable interaction of RNAP with promoter DNA—preventing either DNA binding, DNA retention, or both (sample data in FIG. 8).

b. Myx Prevents Stable Interaction with the Promoter-DNA Segment that Binds within the RNAP Active-Center Cleft.

Figure 9:
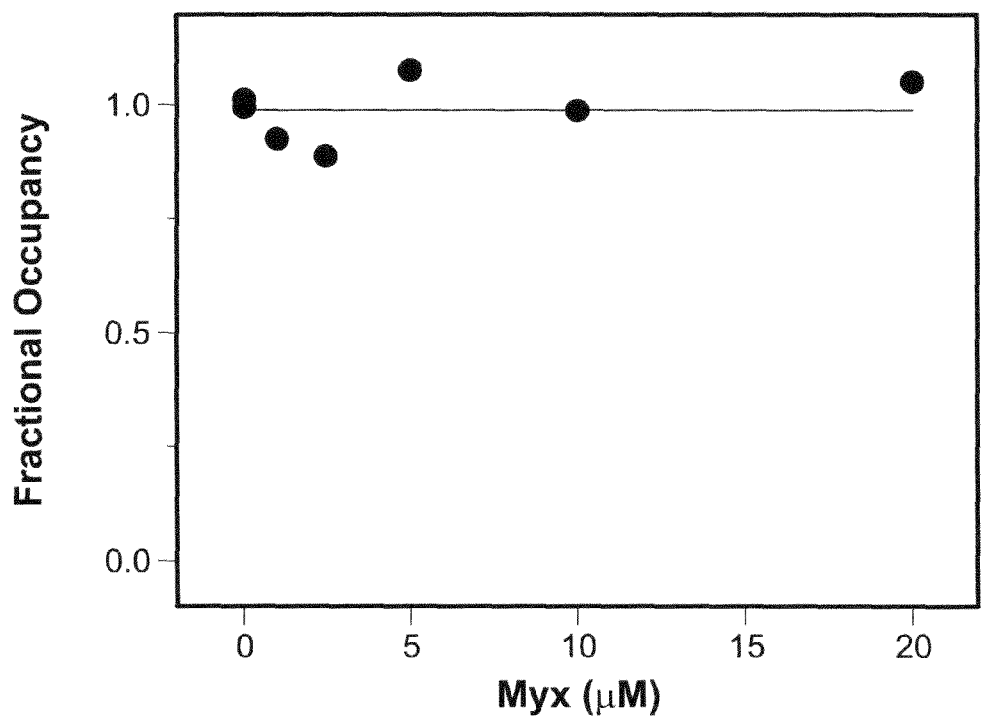
FIG. 9 presents results indicating that Myx does not inhibit interaction of *Escherichia coli* RNAP with the promoter DNA segment comprising positions −40 to −12 (fluorescence-detected electrophoretic mobility shift assays; methods as in Mukhopadhyay, et al. (2004) *Mol. Cell.* 14, 739-751). (A) DNA construct SEQ ID NO:134. (B) Data.

Applicant has performed DNA binding experiments with a series of subfragments of promoter DNA in order to map the interaction of RNAP with promoter DNA inhibited by Myx (methods as in Mukhopadhyay, et al. (2004) *Mol. Cell.* 14, 739-751). The results indicate that Myx inhibits interaction of RNAP with the segment of promoter DNA comprising positions −11 to +15 relative to the transcription start site (sample data in FIG. 9). This DNA segment corresponds, precisely, to the DNA segment proposed to bind within the RNAP active-center cleft, and to be affected by clamp opening and closing, in structural models of transcription initiation complexes (see Ebright (2000) *J. Mol. Biol.* 304, 687-698; Murakami, et al. (2003) *Curr. Opin. Stuct. Biol.* 12, 89-97; Borukhov & Nudler (2003) *Curr. Opin. Microbiol.* 6, 93-100; Murakami, et al. (2002) *Science* 296, 1285-1290; Naryshkin, et al. (2000) *Cell* 101, 601-611; Mekler, et al. (2002) *Cell* 108, 599-614).

3. Myx: Crystal Structure of RNAP-Myx Complex

Applicant has determined a crystal structure of *T. thermophilus* RNAP holoenzyme in complex with Myx. (Myx inhibits *T. thermophilus* RNAP holoenzyme with $K_i$ =20 μM; unpublished data). Crystals of RNAP-Myx were obtained by soaking pre-existing crystals of *T. thermophilus* RNAP holoenzyme in solutions containing Myx, x-ray diffraction data were collected at the Brookhaven National Light Source beamline X-25, and the structure was solved by molecular replacement (methods as in Tuske, et al. (2005) *Cell* 122, 541-552). The crystal structure has a resolution of 3.0 Å (97.1% complete), an R factor of =0.253, and a free R factor of 0.289.

Figure 10:
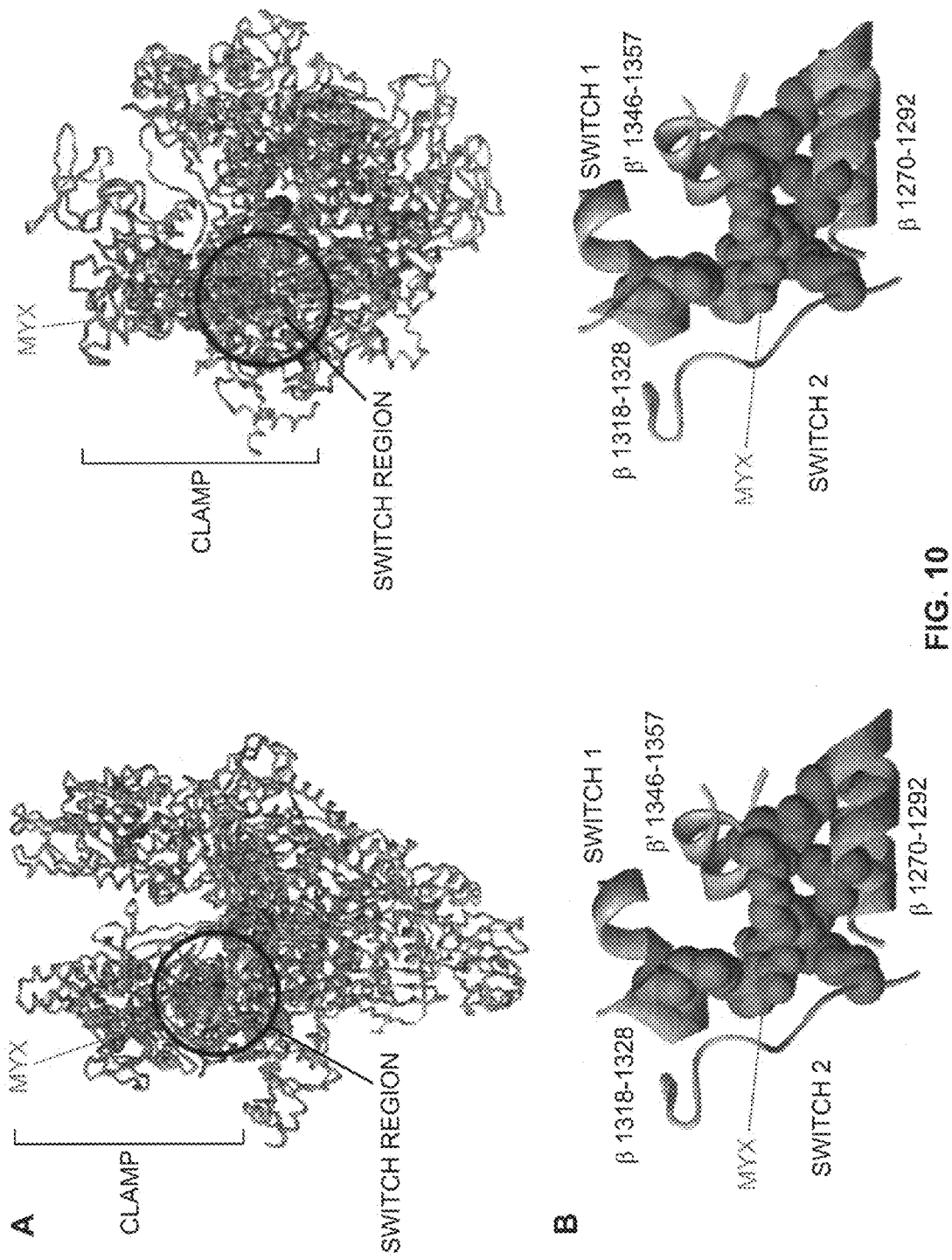
FIG. 10 shows the crystal structure of the *Thermus thermophilus* RNAP-Myx complex. (A) Overall structure of the RNAP-Myx complex (β' nonconserved domain and a omitted for clarity). Green, Myx; violet sphere, active-center $Mg^{2+}$. Two orthogonal views: at left, view through the RNAP active-center cleft; at right, view directly into the RNAP active-center cleft. (B) Stereoview showing details of interactions between the bacterial RNAP homologous switch-region amino-acid sequence and Myx. Blue, RNAP (ribbon representation of RNAP backbone atoms); green, Myx; red, sites of single-residue substitutions that confer high-level resistance to Myx.

The crystal structure defines the binding site for Myx (FIG. 10A), defines interactions between Myx and the binding site (FIG. 10B), and provides a starting point for structure-based screening and structure-based design for identification of new switch-region-target inhibitors. The crystal structure establishes that Myx binds within the bacterial RNAP switch region, and, in particular, within the bacterial'RNAP homologous switch-region amino-acid sequence (FIG. 10). Myx makes direct interactions with the structural elements known as "switch 2" and "switch 1" (FIG. 10B; β' residues 330-347 and 1319-1328, numbered as in *Escherichia coli* RNAP), and also makes direct interactions with adjacent segments of the β' and β subunits (FIG. 10B; β' residues 1346-1357 and β residues 1270-1292 and 1318-1328, numbered as in *Escherichia coli* RNAP). The interactions encompass all four segments of the bacterial RNAP homologous switch-region amino acid sequence (β' residues 345 and 1351, and β residues 1275-1292 and 1322-1326, numbered as in *Escherichia coli* RNAP; FIG. 10B). The interactions with switch 2 and switch 1 involve residues conserved both in bacterial RNAP and in eukaryotic RNAP I, RNAP II, and RNAP III; the interactions with adjacent segments of β' and β involve residues conserved in bacterial RNAP but not conserved in eukaryotic RNAP I, RNAP II, or RNAP III, consistent with the selectivity of Myx. Myx directly contacts all residues at which substitutions conferring high-level Myx resistance are obtained (FIG. 10B).

Myx does not overlap the RNAP active center cleft or the predicted positions of nucleic acids in transcription initiation and elongation complexes (FIG. 10A; Murakami, et al. (2002) *Science* 296, 1285-1290; Gnatt, et al. (2001) *Science* 292, 1876-1882; Westover, et al. (2004a) *Science* 303, 1014-1016; Westover, et al. (2004b) *Cell* 119, 481-489; Kettenberger, et al. (2004) *Mol. Cell.* 16, 955-965; Naryshkin, et al. (2000) *Cell* 101, 601-611; Mekler, et al. (2002) *Cell* 108, 599-614). Indeed, Myx is nearly completely buried, with little or no surface accessibility on the interior of the RNAP active-center cleft and with no surface accessibility on the on the exterior of RNAP (FIG. 10A). These observations suggest that Myx inhibits transcription through allosteric interactions, not through direct, steric interactions.

The RNAP clamp in the crystal structure of RNAP-Myx adopts the same conformation as in the crystal structure of unliganded RNAP in the same crystal form (FIG. 10A; compare FIG. 1A): i.e., an intermediate clamp conformation. This observation permits the conclusion that binding of Myx is compatible with an intermediate clamp conformation. However, this observation does not permit the conclusion that binding of Myx favors, stabilizes, or induces an intermediate clamp conformation, since clamp conformation in the crystal is constrained by, and may be determined by, crystal-lattice interactions.

The RNAP switch region in the crystal structure of RNAP-Myx adopts a different conformation from that in the crystal structure of unliganded RNAP in the same crystal form. The difference in conformation involves a seven-residue segment of switch 2—a seven-residue segment that differs in conformation in open-clamp, intermediate-clamp, and closed-clamp conformational states (FIG. 1B; β' residues 337-343, numbered as in *Escherichia coli* RNAP). The difference in conformation involves 1-4 Å displacements of Cα atoms of the seven-residue segment toward positions characteristic of those in the closed-clamp conformational state.

4. Myx: Working Hypothesis

While not wishing to be bound by any one hypothesis, Applicant infers from the genetic, biochemical, and structural results described above, that Myx may inhibit transcription by locking the RNAP switch region in one conformational state, preventing switch-region conformational cycling, and thereby rendering the RNAP clamp unable to open to permit entry of DNA into the RNAP active-center cleft, unable to close to permit retention of DNA within the RNAP-active-center cleft, or both.

Example 2

Switch-Region-Target Inhibitors: COR

The present example is directed to the use of corallopyronin (Cor) as a small-molecule inhibitor of RNAP that, based on Applicant's discovery, inhibits RNAP through interaction with the bacterial RNAP homologous switch-region amino-acid sequence. Cor is a polyketide-derived α-pyrone antibiotic structurally related to Myx, differing only by possession of a seven-carbon side-chain extension (Irschik, et al. (1985) *J. Antibiot.* 38, 145-152; FIG. 4A,B). Cor is produced by the myxobacterium *Corallococcus coralloides* strain Cc c127 (DSM 2550; Irschik, et al. (1985) Supra). The compound potently inhibits growth of Gram-positive and Gram-negative bacterial species, including *Bacillus subtilis, B. megaterium, S. aureus, M. luteus, C. mediolanum,* and *Escherichia coli* DH21tolC (MICs≦10 µg/ml for all; MIC≦0.1 µg/ml for *S. aureus*; Irschik, et al. (1985) Supra; unpublished data). The compound is bacteriocidal, as assessed in experiments with *Escherichia coli* DH21tolC (unpublished data). The compound inhibits bacterial RNAP ($K_i$=4 µM) but does not inhibit eukaryotic RNAP II (Irschik, et al. (1985) *J. Antibiot.* 38, 145-152). The compound exhibits no cross-resistance with rifamycins, CBR-703, or microcin J25 (O'Neill, et al. (2000) *Antimicrob. Agents Chemother* 44, 3163-3166; unpublished data).

Applicant has tested Myx-resistant mutants for cross-resistance to the structurally related antibiotic Cor and has performed saturation mutagenesis and directly isolated and characterized more than 75 independent Cor-resistant mutants (methods as in Example 1, employing the "doped" oligodeoxyribonucleotide primers in Table 2). The results, presented in Tables 4 and 5, establish that Cor functions through interactions with the same target as Myx: i.e., a target encompassing the bacterial RNAP homologous switch-region amino-acid sequence. In addition, by defining a residue that interacts with the seven-carbon-atom side-chain extension present in Cor but absent in Myx (β residue 1326, numbered as in *Escherichia coli* RNAP), the results define the binding orientation of the ligand relative to the target, providing independent support for the binding orientation observed in the crystal structure of the RNAP-Myx complex.

Applicant also has assessed effects of Cor on transcription, promoter binding, and promoter-subfragment binding (methods as in Example 1). The results (not shown) establish that Cor functions through the same mechanism as Myx.

TABLE 4

Myx/Cor/Rip cross-resistance patterns

| amino acid substitution | selected resistance(s) | MIC ratio (MIC, mutant/MIC, wild-type) Myx | Cor | Rip |
|---|---|---|---|---|
| rpoC single-substitution mutants | | | | |
| 345 Lys→Arg | Myx, Cor, Rip | >32 | >8 | >16 |
| 345 Lys→Asn | Myx, Cor | 32 | 8 | 8 |
| 345 Lys→Thr | Myx, Cor | 32 | 8 | >16 |
| 1346 Gly→Asp | Cor | 1 | 4 | 4 |
| 1351 Val→Phe | Myx, Cor, Rip | >32 | >8 | >16 |
| 1352 Ile→Asn | Rip | 2 | 4 | >16 |
| 1352 Ile→Ser | Rip | 2 | 4 | >16 |
| 1354 Gly→Cys | Cor | 2 | 2 | 4 |
| rpoB single-substitution mutants | | | | |
| 1255 Thr→Ile | Myx | 2 | 4 | 4 |
| 1275 Val→Met | Myx, Cor | >32 | >8 | 8 |
| 1275 Val→Phe | Myx | >32 | >8 | >16 |
| 1278 Leu→Val | Myx | 2 | 4 | >16 |
| 1279 Glu→Gly | Rip | 32 | 4 | >16 |
| 1279 Glu→Lys | Myx, Cor | >32 | 8 | 4 |
| 1283 Ala→Val | Rip | 2 | 4 | 4 |
| 1285 Tyr→Asp | Myx | 2 | 1 | 4 |
| 1291 Leu→Phe | Myx, Rip | 2 | 1 | 4 |
| 1298 Val→Leu | Myx | 2 | 2 | 4 |
| 1315 Met→Leu | Myx | 2 | 2 | 4 |
| 1317 Pro→Leu | Myx | 2 | 2 | 2 |
| 1320 Pro→Ala | Myx | 2 | 4 | 4 |
| 1322 Ser→Pro | Rip | 32 | 4 | >16 |
| 1322 Ser→Thr | Myx | 2 | 4 | 4 |
| 1322 Ser→Tyr | Myx | 2 | 4 | 2 |
| 1322 Ser→Val | Myx | 16 | 8 | >16 |
| 1325 Val→Leu | Myx | 2 | 4 | 4 |
| 1326 Leu→Trp | Rip | 1 | >8 | >16 |

TABLE 5

$Cor^r$ isolates from saturation mutagenesis and selection

| amino acid substitution | number of independent isolates | MIC ratio |
|---|---|---|
| rpoC | | |
| 345 Lys→Arg | 2 | >8 |
| 345 Lys→Asn | 13 | 8 |
| 345 Lys→Gln | 2 | |
| 345 Lys→Thr | 3 | 8 |
| 1346 Gly→Asp | 1 | 4 |
| 1351 Val→Phe | 15 | >8 |
| 1354 Gly→Cys | 2 | 2 |
| rpoB single-substitution mutants | | |
| 1275 Val→Met | 26 | >8 |
| 1279 Glu→Lys | 11 | 8 |
| Multiple-substitution mutants | | |
| 1232 Met→Ile; 1275 Val→Met | 1 | |
| 1279 Glu→Lys; 1285 Tyr→Gly | 1 | |
| 1279 Glu→Lys; 1287 Leu→Gln | 1 | |

Example 3

Switch-Region-Target Inhibitors: RIP

The present example is directed to the use of ripostatin (Rip) as a small-molecule inhibitor of RNAP that, based on Applicant's discovery, inhibits RNAP through interactions with the bacterial RNAP homologous switch-region amino-acid sequence. Rip is a polyketide-derived macrocylic-lactone antibiotic (Irschik, et al. (1995) *J. Anitibiol.* 48, 787-792; Augustiniak, et al. (1996) *Liebigs Ann.* 10, 1657-1663); FIG. 4C). Rip is produced by the myxobacterium *Sorangium cellulosum* strain So ce377 (DSM 7291; Irschik, et al. (1995) Supra). The compound potently inhibits growth of Gram-positive and Gram-negative bacterial species, including *S. aureus*, and *Escherichia coli* DH21tolC (MICs$\leqq$1 μg/ml; Irschik, et al. (1995) Supra; unpublished data). The compound is bacteriocidal, as assessed in experiments with *Escherichia coli* DH21 tolC (unpublished data). The compound inhibits bacterial RNAP ($K_i$=0.3 μM) but does not inhibit eukaryotic RNAP II (Irschik, et al. (1995) Supra). The compound exhibits no cross-resistance with rifamycins, CBR-703, or microcin J25 (O'Neill, et al. (2000) *Antimicrob. Agents Chemother.* 44, 3163-3166; Irschik, et al. (1995) Supra; unpublished data).

Applicant has tested Myx-resistant mutants for cross-resistance to the structurally unrelated antibiotic Rip and has performed saturation mutagenesis and directly isolated and characterized more than 50 independent Rip-resistant mutants (methods as in Example 1, employing the "doped" oligodeoxyribonucleotide primers in Table 2). The results, presented in Tables 4 and 6, establish that, surprisingly, in view of its very different chemical structure (FIG. 4C; compare FIG. 4A), Rip functions through interactions with the same target as Myx: i.e., a target encompassing the bacterial RNAP homologous switch-region amino-acid sequence. Applicant also has assessed effects of Rip on transcription, promoter binding, and promoter-subfragment binding (methods as in Example 1). The results (not shown) establish that, surprisingly, in view of its very different chemical structure (FIG. 4C; compare FIG. 4A), Rip functions through the same mechanism as Myx.

TABLE 6

$Rip^r$ isolates from saturation mutagenesis and selection

| amino acid substitution | number of independent isolates | MIC ratio |
|---|---|---|
| rpoC single-substitution mutants | | |
| 345 Lys→Arg | 7 | >16 |
| 1351 Val→Phe | 9 | >16 |
| 1352 Ile→Asn | 9 | >16 |
| 1352 Ile→Ser | 5 | >16 |
| multiple-substitution mutants | | |
| 1349 Glu→Asp; 1351 Val→Phe | 1 | |
| 1349 Glu→Asp; 1352 Ile→Ser | 3 | |
| 1350 Asn→Tyr; 1351 Val→Phe | 2 | |
| 1351 Val→Phe; 1354 Gly→Cys | 1 | |
| 1351 Val→Phe; 1356 Leu→Pro | 1 | |
| rpoB single-substitution mutants | | |
| 1279 Glu→Gly | 1 | >16 |
| 1283 Ala→Val | 1 | 4 |
| 1291 Leu→Phe | 1 | 4 |
| 1322 Ser→Pro | 2 | >16 |
| 1326 Leu→Trp | 6 | >16 |
| multiple-substitution mutants | | |
| 1279 Glu→Val; 1283 Ala→Val | 2 | |
| 1322 Ser→Pro; 1325 Val→Gly | 1 | |
| 1323 Phe→Cys; 1326 Leu→Trp | 2 | |
| 1328 Lys→Thr | | |

TABLE 6-continued

Rip<sup>r</sup> isolates from saturation mutagenesis and selection

| amino acid substitution | number of independent isolates | MIC ratio |
|---|---|---|
| 1291 Leu→Phe; 1319 Met→Ile 1320 Pro→Ser; 1321 Glu→Lys | 1 | |

Example 4

High-Throughput Assay for Switch-Region-Target Inhibitors

Applicant has developed and demonstrated a microplate-based high-throughput assay for switch-region-target inhibitors. The assay employs measurement of fluorescence-detected abortive initiation (methods analogous to those described in Mukhopadhyay, et al, (2004) *Mol. Cell.* 14, 739-751; Tuske, et al. (2005) *Cell* 122, 541-552; see also Schlageck, et al., (1979) *J. Biol. Chem.* 254, 12074-12077). The assay involves two measurements performed in parallel: (i) measurement of effects on transcription by wild-type *Escherichia coli* RNAP, and (ii) measurement of effects on transcription by [Arg345]β'-RNAP, an RNAP derivative having a substitution within the switch-region target that confers high-level resistance to Myx, Cor, and Rip. Switch-region-target inhibitors are identifiable as compounds that in

```
<212> TYPE: PRT
<213> ORGANISM: Escherichia coli

<400> SEQUENCE: 4

Met Glu Val Trp Ala Leu Glu Ala Tyr Gly Ala Ala Tyr Thr Leu Gln
1               5                   10                  15

Glu Met Leu Thr Val Lys Ser Asp Asp Val Asn Gly
            20                  25

<210> SEQ ID NO 5
<211> LENGTH: 13
<212> TYPE: PRT
<213> ORGANISM: Escherichia coli

<400> SEQUENCE: 5

Gly Met Pro Glu Ser Phe Asn Val Leu Leu Lys Glu Ile
1               5                   10

<210> SEQ ID NO 6
<211> LENGTH: 7
<212> TYPE: PRT
<213> ORGANISM: Haemophilus influenzae

<400> SEQUENCE: 6

Leu Leu Gly Lys Arg Val Asp
1               5

<210> SEQ ID NO 7
<211> LENGTH: 14
<212> TYPE: PRT
<213> ORGANISM: Haemophilus influenzae

<400> SEQUENCE: 7

Gly Leu Lys Glu Asn Val Ile Val Gly Arg Leu Ile Pro Ala
1               5                   10

<210> SEQ ID NO 8
<211> LENGTH: 5
<212> TYPE: PRT
<213> ORGANISM: Haemophilus influenzae

<400> SEQUENCE: 8

Ser Ile Val Thr Gln
1               5

<210> SEQ ID NO 9
<211> LENGTH: 28
<212> TYPE: PRT
<213> ORGANISM: Haemophilus influenzae

<400> SEQUENCE: 9

Met Glu Val Trp Ala Leu Glu Ala Tyr Gly Ala Ala Tyr Thr Leu Gln
1               5                   10                  15

Glu Met Leu Thr Val Lys Ser Asp Asp Val Asn Gly
            20                  25

<210> SEQ ID NO 10
<211> LENGTH: 13
<212> TYPE: PRT
<213> ORGANISM: Haemophilus influenzae

<400> SEQUENCE: 10

Gly Thr Pro Glu Ser Phe Asn Val Ile Met Lys Glu Ile
1               5                   10
```

```
<210> SEQ ID NO 11
<211> LENGTH: 7
<212> TYPE: PRT
<213> ORGANISM: Vibrio cholerae

<400> SEQUENCE: 11

Leu Leu Gly Lys Arg Val Asp
1               5

<210> SEQ ID NO 12
<211> LENGTH: 14
<212> TYPE: PRT
<213> ORGANISM: Vibrio cholerae

<400> SEQUENCE: 12

Gly Leu Lys Glu Asn Val Ile Val Gly Arg Leu Ile Pro Ala
1               5                   10

<210> SEQ ID NO 13
<211> LENGTH: 5
<212> TYPE: PRT
<213> ORGANISM: Vibrio cholerae

<400> SEQUENCE: 13

Ser Ile Val Thr Gln
1               5

<210> SEQ ID NO 14
<211> LENGTH: 28
<212> TYPE: PRT
<213> ORGANISM: Vibrio cholerae

<400> SEQUENCE: 14

Met Glu Val Trp Ala Leu Glu Ala Tyr Gly Ala Ala Tyr Thr Leu Gln
1               5                   10                  15

Glu Met Leu Thr Val Lys Ser Asp Asp Val Asn Gly
            20                  25

<210> SEQ ID NO 15
<211> LENGTH: 13
<212> TYPE: PRT
<213> ORGANISM: Vibrio cholerae

<400> SEQUENCE: 15

Gly Met Pro Glu Ser Phe Asn Val Leu Leu Lys Glu Ile
1               5                   10

<210> SEQ ID NO 16
<211> LENGTH: 7
<212> TYPE: PRT
<213> ORGANISM: Pseudomonas aeruginosa

<400> SEQUENCE: 16

Leu Leu Gly Lys Arg Val Asp
1               5

<210> SEQ ID NO 17
<211> LENGTH: 14
<212> TYPE: PRT
<213> ORGANISM: Pseudomonas aeruginosa

<400> SEQUENCE: 17

Gly Leu Lys Glu Asn Val Val Val Gly Arg Leu Ile Pro Ala
1               5                   10
```

```
<210> SEQ ID NO 18
<211> LENGTH: 5
<212> TYPE: PRT
<213> ORGANISM: Pseudomonas aeruginosa

<400> SEQUENCE: 18

Ser Ile Val Thr Gln
1               5

<210> SEQ ID NO 19
<211> LENGTH: 28
<212> TYPE: PRT
<213> ORGANISM: Pseudomonas aeruginosa

<400> SEQUENCE: 19

Met Glu Val Trp Ala Leu Glu Ala Tyr Gly Ala Ala Tyr Thr Leu Gln
1               5                   10                  15

Glu Met Leu Thr Val Lys Ser Asp Asp Val Asn Gly
            20                  25

<210> SEQ ID NO 20
<211> LENGTH: 13
<212> TYPE: PRT
<213> ORGANISM: Pseudomonas aeruginosa

<400> SEQUENCE: 20

Gly Met Pro Glu Ser Phe Asn Val Leu Ile Lys Glu Ile
1               5                   10

<210> SEQ ID NO 21
<211> LENGTH: 7
<212> TYPE: PRT
<213> ORGANISM: Treponema pallidum

<400> SEQUENCE: 21

Leu Leu Gly Lys Arg Val Asp
1               5

<210> SEQ ID NO 22
<211> LENGTH: 14
<212> TYPE: PRT
<213> ORGANISM: Treponema pallidum

<400> SEQUENCE: 22

Gly Leu Lys Glu Asn Val Ile Ile Gly His Leu Ile Pro Ala
1               5                   10

<210> SEQ ID NO 23
<211> LENGTH: 5
<212> TYPE: PRT
<213> ORGANISM: Treponema pallidum

<400> SEQUENCE: 23

Ser Ile Val Thr Gln
1               5

<210> SEQ ID NO 24
<211> LENGTH: 28
<212> TYPE: PRT
<213> ORGANISM: Treponema pallidum

<400> SEQUENCE: 24

Met Glu Val Trp Ala Leu Glu Ala Tyr Gly Ala Ala Asn Thr Leu Gln
1               5                   10                  15
```

-continued

```
Glu Leu Leu Thr Ile Lys Ser Asp Asp Met His Gly
            20                  25

<210> SEQ ID NO 25
<211> LENGTH: 13
<212> TYPE: PRT
<213> ORGANISM: Treponema pallidum

<400> SEQUENCE: 25

Gly Ile Pro Glu Ser Phe Asn Val Leu Val Gln Glu Leu
1               5                   10

<210> SEQ ID NO 26
<211> LENGTH: 7
<212> TYPE: PRT
<213> ORGANISM: Borrelia burgdorferi

<400> SEQUENCE: 26

Leu Leu Gly Lys Arg Val Asp
1               5

<210> SEQ ID NO 27
<211> LENGTH: 14
<212> TYPE: PRT
<213> ORGANISM: Borrelia burgdorferi

<400> SEQUENCE: 27

Gly Leu Lys Glu Asn Val Val Ile Gly His Leu Ile Pro Thr
1               5                   10

<210> SEQ ID NO 28
<211> LENGTH: 5
<212> TYPE: PRT
<213> ORGANISM: Borrelia burgdorferi

<400> SEQUENCE: 28

Ser Ile Val Ser Gln
1               5

<210> SEQ ID NO 29
<211> LENGTH: 28
<212> TYPE: PRT
<213> ORGANISM: Borrelia burgdorferi

<400> SEQUENCE: 29

Met Glu Val Trp Ala Leu Glu Ala Tyr Gly Ala Ala His Thr Leu Gln
1               5                   10                  15

Glu Leu Leu Thr Val Lys Ser Asp Asp Met Ser Gly
            20                  25

<210> SEQ ID NO 30
<211> LENGTH: 13
<212> TYPE: PRT
<213> ORGANISM: Borrelia burgdorferi

<400> SEQUENCE: 30

Gly Ile Pro Glu Ser Phe Asn Val Leu Met Gln Glu Leu
1               5                   10

<210> SEQ ID NO 31
<211> LENGTH: 7
<212> TYPE: PRT
<213> ORGANISM: Xylella fastidiosa

<400> SEQUENCE: 31
```

```
Leu Leu Gly Lys Arg Val Asp
1               5

<210> SEQ ID NO 32
<211> LENGTH: 14
<212> TYPE: PRT
<213> ORGANISM: Xylella fastidiosa

<400> SEQUENCE: 32

Gly Leu Lys Glu Asn Val Ile Val Gly Arg Leu Ile Pro Ala
1               5                   10

<210> SEQ ID NO 33
<211> LENGTH: 5
<212> TYPE: PRT
<213> ORGANISM: Xylella fastidiosa

<400> SEQUENCE: 33

Ser Ile Val Thr Gln
1               5

<210> SEQ ID NO 34
<211> LENGTH: 28
<212> TYPE: PRT
<213> ORGANISM: Xylella fastidiosa

<400> SEQUENCE: 34

Met Glu Val Trp Ala Leu Glu Ala Tyr Gly Ala Ala Tyr Thr Leu Gln
1               5                   10                  15

Glu Met Leu Thr Val Lys Ser Asp Asp Val Gln Gly
            20                  25

<210> SEQ ID NO 35
<211> LENGTH: 13
<212> TYPE: PRT
<213> ORGANISM: Xylella fastidiosa

<400> SEQUENCE: 35

Gly Met Pro Glu Ser Phe Asn Val Leu Val Lys Glu Ile
1               5                   10

<210> SEQ ID NO 36
<211> LENGTH: 7
<212> TYPE: PRT
<213> ORGANISM: Campylobacter jejuni

<400> SEQUENCE: 36

Leu Leu Gly Lys Arg Val Asp
1               5

<210> SEQ ID NO 37
<211> LENGTH: 14
<212> TYPE: PRT
<213> ORGANISM: Campylobacter jejuni

<400> SEQUENCE: 37

Asp Leu Lys Glu Asn Val Ile Leu Gly Arg Met Ile Pro Val
1               5                   10

<210> SEQ ID NO 38
<211> LENGTH: 5
<212> TYPE: PRT
<213> ORGANISM: Campylobacter jejuni

<400> SEQUENCE: 38
```

Ser Leu Val Thr Gln
1               5

<210> SEQ ID NO 39
<211> LENGTH: 28
<212> TYPE: PRT
<213> ORGANISM: Campylobacter jejuni

<400> SEQUENCE: 39

Met Glu Val Trp Ala Leu Glu Ala Tyr Gly Ala Ala His Thr Leu Arg
1               5                   10                  15

Glu Met Leu Thr Ile Lys Ser Asp Asp Val Glu Gly
            20                  25

<210> SEQ ID NO 40
<211> LENGTH: 13
<212> TYPE: PRT
<213> ORGANISM: Campylobacter jejuni

<400> SEQUENCE: 40

Gly Ile Pro Glu Thr Phe Glu Val Leu Thr Asn Glu Leu
1               5                   10

<210> SEQ ID NO 41
<211> LENGTH: 7
<212> TYPE: PRT
<213> ORGANISM: Neisseria meningitidis

<400> SEQUENCE: 41

Leu Leu Gly Lys Arg Val Asp
1               5

<210> SEQ ID NO 42
<211> LENGTH: 14
<212> TYPE: PRT
<213> ORGANISM: Neisseria meningitidis

<400> SEQUENCE: 42

Gly Leu Lys Glu Asn Val Ile Val Gly Arg Leu Ile Pro Ala
1               5                   10

<210> SEQ ID NO 43
<211> LENGTH: 5
<212> TYPE: PRT
<213> ORGANISM: Neisseria meningitidis

<400> SEQUENCE: 43

Ser Ile Val Thr Gln
1               5

<210> SEQ ID NO 44
<211> LENGTH: 28
<212> TYPE: PRT
<213> ORGANISM: Neisseria meningitidis

<400> SEQUENCE: 44

Met Glu Val Trp Ala Leu Glu Ala Tyr Gly Ala Ala Tyr Thr Leu Gln
1               5                   10                  15

Glu Met Leu Thr Val Lys Ser Asp Asp Val Asn Gly
            20                  25

<210> SEQ ID NO 45
<211> LENGTH: 13
<212> TYPE: PRT
<213> ORGANISM: Neisseria meningitidis

<400> SEQUENCE: 45

Gly Met Pro Glu Ser Phe Asn Val Leu Val Lys Glu Ile
1               5                   10

<210> SEQ ID NO 46
<211> LENGTH: 7
<212> TYPE: PRT
<213> ORGANISM: Rickettsia prowazekii

<400> SEQUENCE: 46

Leu Leu Gly Lys Arg Val Asp
1               5

<210> SEQ ID NO 47
<211> LENGTH: 14
<212> TYPE: PRT
<213> ORGANISM: Rickettsia prowazekii

<400> SEQUENCE: 47

Gly Lys Leu Glu Asn Val Ile Val Gly Arg Leu Val Pro Ala
1               5                   10

<210> SEQ ID NO 48
<211> LENGTH: 5
<212> TYPE: PRT
<213> ORGANISM: Rickettsia prowazekii

<400> SEQUENCE: 48

Ser Ile Val Thr Gln
1               5

<210> SEQ ID NO 49
<211> LENGTH: 28
<212> TYPE: PRT
<213> ORGANISM: Rickettsia prowazekii

<400> SEQUENCE: 49

Met Glu Cys Trp Ala Leu Gln Ala Tyr Gly Ala Ala Tyr Thr Leu Gln
1               5                   10                  15

Glu Met Leu Thr Val Lys Ser Asp Asp Val Asn Gly
            20                  25

<210> SEQ ID NO 50
<211> LENGTH: 13
<212> TYPE: PRT
<213> ORGANISM: Rickettsia prowazekii

<400> SEQUENCE: 50

Gly Ile Pro Glu Ser Phe Asn Val Met Ile Lys Glu Phe
1               5                   10

<210> SEQ ID NO 51
<211> LENGTH: 7
<212> TYPE: PRT
<213> ORGANISM: Chlamydia trachomatis

<400> SEQUENCE: 51

Leu Leu Gly Lys Arg Val Asp
1               5

<210> SEQ ID NO 52
<211> LENGTH: 14
<212> TYPE: PRT
<213> ORGANISM: Chlamydia trachomatis

```
<400> SEQUENCE: 52

Gly Phe Lys Glu Asn Val Ile Met Gly His Met Ile Pro Gly
1               5                   10

<210> SEQ ID NO 53
<211> LENGTH: 5
<212> TYPE: PRT
<213> ORGANISM: Chlamydia trachomatis

<400> SEQUENCE: 53

Ser Leu Val Thr Gln
1               5

<210> SEQ ID NO 54
<211> LENGTH: 28
<212> TYPE: PRT
<213> ORGANISM: Chlamydia trachomatis

<400> SEQUENCE: 54

Met Glu Val Trp Ala Leu Glu Ala Tyr Gly Val Ala His Met Leu Gln
1               5                   10                  15

Glu Ile Leu Thr Val Lys Ser Asp Asp Val Ser Gly
            20                  25

<210> SEQ ID NO 55
<211> LENGTH: 13
<212> TYPE: PRT
<213> ORGANISM: Chlamydia trachomatis

<400> SEQUENCE: 55

Gly Thr Pro Glu Ser Phe Asn Val Leu Ile Lys Glu Met
1               5                   10

<210> SEQ ID NO 56
<211> LENGTH: 7
<212> TYPE: PRT
<213> ORGANISM: Mycoplasma pneumoniae

<400> SEQUENCE: 56

Leu Leu Gly Lys Arg Val Asp
1               5

<210> SEQ ID NO 57
<211> LENGTH: 14
<212> TYPE: PRT
<213> ORGANISM: Mycoplasma pneumoniae

<400> SEQUENCE: 57

Gly Lys Leu Glu Asn Val Ile Ile Gly Gly Lys Ile Pro Ala
1               5                   10

<210> SEQ ID NO 58
<211> LENGTH: 5
<212> TYPE: PRT
<213> ORGANISM: Mycoplasma pneumoniae

<400> SEQUENCE: 58

Ser Lys Ile Thr Gln
1               5

<210> SEQ ID NO 59
<211> LENGTH: 28
<212> TYPE: PRT
<213> ORGANISM: Mycoplasma pneumoniae
```

```
<400> SEQUENCE: 59

Met Glu Val Trp Ala Leu Glu Ala Tyr Gly Ala Ala Tyr Asn Leu Gln
1               5                   10                  15

Glu Leu Leu Thr Ile Lys Ser Asp Asp Val Gln Gly
            20                  25

<210> SEQ ID NO 60
<211> LENGTH: 13
<212> TYPE: PRT
<213> ORGANISM: Mycoplasma pneumoniae

<400> SEQUENCE: 60

Gly Ile Pro Glu Ser Phe Lys Leu Leu Thr Lys Glu Leu
1               5                   10

<210> SEQ ID NO 61
<211> LENGTH: 7
<212> TYPE: PRT
<213> ORGANISM: Bacillus subtilis

<400> SEQUENCE: 61

Leu Leu Gly Lys Arg Val Asp
1               5

<210> SEQ ID NO 62
<211> LENGTH: 14
<212> TYPE: PRT
<213> ORGANISM: Bacillus subtilis

<400> SEQUENCE: 62

Gly Leu Lys Glu Asn Val Ile Ile Gly Lys Leu Val Pro Gly
1               5                   10

<210> SEQ ID NO 63
<211> LENGTH: 5
<212> TYPE: PRT
<213> ORGANISM: Bacillus subtilis

<400> SEQUENCE: 63

Ser Ile Val Thr Gln
1               5

<210> SEQ ID NO 64
<211> LENGTH: 28
<212> TYPE: PRT
<213> ORGANISM: Bacillus subtilis

<400> SEQUENCE: 64

Met Glu Val Trp Ala Leu Glu Ala Tyr Gly Ala Ala Tyr Thr Leu Gln
1               5                   10                  15

Glu Ile Leu Thr Val Lys Ser Asp Asp Val Val Gly
            20                  25

<210> SEQ ID NO 65
<211> LENGTH: 13
<212> TYPE: PRT
<213> ORGANISM: Bacillus subtilis

<400> SEQUENCE: 65

Gly Val Pro Glu Ser Phe Lys Val Leu Ile Lys Glu Leu
1               5                   10

<210> SEQ ID NO 66
```

```
<211> LENGTH: 7
<212> TYPE: PRT
<213> ORGANISM: Staphylococcus aureus

<400> SEQUENCE: 66

Leu Leu Gly Lys Arg Val Asp
1               5

<210> SEQ ID NO 67
<211> LENGTH: 14
<212> TYPE: PRT
<213> ORGANISM: Staphylococcus aureus

<400> SEQUENCE: 67

Gly Leu Lys Glu Asn Val Ile Ile Gly Lys Leu Ile Pro Ala
1               5                   10

<210> SEQ ID NO 68
<211> LENGTH: 5
<212> TYPE: PRT
<213> ORGANISM: Staphylococcus aureus

<400> SEQUENCE: 68

Ser Ile Val Thr Gln
1               5

<210> SEQ ID NO 69
<211> LENGTH: 28
<212> TYPE: PRT
<213> ORGANISM: Staphylococcus aureus

<400> SEQUENCE: 69

Met Glu Val Trp Ala Leu Glu Ala Tyr Gly Ala Ala Tyr Thr Leu Gln
1               5                   10                  15

Glu Ile Leu Thr Tyr Lys Ser Asp Asp Thr Val Gly
            20                  25

<210> SEQ ID NO 70
<211> LENGTH: 13
<212> TYPE: PRT
<213> ORGANISM: Staphylococcus aureus

<400> SEQUENCE: 70

Ser Val Pro Glu Ser Phe Arg Val Leu Met Lys Glu Leu
1               5                   10

<210> SEQ ID NO 71
<211> LENGTH: 7
<212> TYPE: PRT
<213> ORGANISM: Mycobacterium tuberculosis

<400> SEQUENCE: 71

Leu Leu Gly Lys Arg Val Asp
1               5

<210> SEQ ID NO 72
<211> LENGTH: 14
<212> TYPE: PRT
<213> ORGANISM: Mycobacterium tuberculosis

<400> SEQUENCE: 72

Gly Leu Lys Glu Asn Val Ile Ile Gly Lys Leu Ile Pro Ala
1               5                   10

<210> SEQ ID NO 73
```

```
<211> LENGTH: 5
<212> TYPE: PRT
<213> ORGANISM: Mycobacterium tuberculosis

<400> SEQUENCE: 73

Ser Met Ile Thr Gln
1               5

<210> SEQ ID NO 74
<211> LENGTH: 28
<212> TYPE: PRT
<213> ORGANISM: Mycobacterium tuberculosis

<400> SEQUENCE: 74

Met Glu Cys Trp Ala Met Gln Ala Tyr Gly Ala Ala Tyr Thr Leu Gln
1               5                   10                  15

Glu Leu Leu Thr Ile Lys Ser Asp Asp Thr Val Gly
            20                  25

<210> SEQ ID NO 75
<211> LENGTH: 13
<212> TYPE: PRT
<213> ORGANISM: Mycobacterium tuberculosis

<400> SEQUENCE: 75

Gly Ile Pro Glu Ser Phe Lys Val Leu Leu Lys Glu Leu
1               5                   10

<210> SEQ ID NO 76
<211> LENGTH: 7
<212> TYPE: PRT
<213> ORGANISM: Synechocystis sp.

<400> SEQUENCE: 76

Leu Leu Gly Lys Arg Val Asp
1               5

<210> SEQ ID NO 77
<211> LENGTH: 14
<212> TYPE: PRT
<213> ORGANISM: Synechocystis sp.

<400> SEQUENCE: 77

Gly Leu Lys Glu Asn Val Ile Ile Gly Arg Leu Ile Pro Ala
1               5                   10

<210> SEQ ID NO 78
<211> LENGTH: 5
<212> TYPE: PRT
<213> ORGANISM: Synechocystis sp.

<400> SEQUENCE: 78

Ser Ile Val Thr Gln
1               5

<210> SEQ ID NO 79
<211> LENGTH: 28
<212> TYPE: PRT
<213> ORGANISM: Synechocystis sp.

<400> SEQUENCE: 79

Met Glu Val Trp Ala Leu Glu Ala Tyr Gly Ala Ala Tyr Ile Leu Gln
1               5                   10                  15

Glu Leu Leu Thr Val Lys Ser Asp Asp Met Gln Gly
            20                  25
```

```
<210> SEQ ID NO 80
<211> LENGTH: 13
<212> TYPE: PRT
<213> ORGANISM: Synechocystis sp.

<400> SEQUENCE: 80

Gly Thr Pro Glu Ser Phe Lys Val Leu Met Arg Glu Leu
1               5                   10

<210> SEQ ID NO 81
<211> LENGTH: 7
<212> TYPE: PRT
<213> ORGANISM: aquifex aeolicus

<400> SEQUENCE: 81

Leu Leu Gly Lys Arg Val Asp
1               5

<210> SEQ ID NO 82
<211> LENGTH: 14
<212> TYPE: PRT
<213> ORGANISM: aquifex aeolicus

<400> SEQUENCE: 82

Gly Leu Lys Glu Asn Val Ile Ile Gly Asn Ile Ile Pro Ala
1               5                   10

<210> SEQ ID NO 83
<211> LENGTH: 5
<212> TYPE: PRT
<213> ORGANISM: aquifex aeolicus

<400> SEQUENCE: 83

Ser Leu Val Thr Gln
1               5

<210> SEQ ID NO 84
<211> LENGTH: 28
<212> TYPE: PRT
<213> ORGANISM: aquifex aeolicus

<400> SEQUENCE: 84

Met Glu Val Trp Ala Leu Glu Ala His Gly Ala Ala Tyr Thr Leu Gln
1               5                   10                  15

Glu Met Leu Thr Val Lys Ser Asp Asp Val Glu Gly
            20                  25

<210> SEQ ID NO 85
<211> LENGTH: 13
<212> TYPE: PRT
<213> ORGANISM: aquifex aeolicus

<400> SEQUENCE: 85

Gly Ile Pro Glu Ser Phe Lys Val Leu Val Arg Glu Leu
1               5                   10

<210> SEQ ID NO 86
<211> LENGTH: 7
<212> TYPE: PRT
<213> ORGANISM: Deinococcus radiodurans

<400> SEQUENCE: 86

Leu Leu Gly Lys Arg Val Asp
1               5
```

```
<210> SEQ ID NO 87
<211> LENGTH: 14
<212> TYPE: PRT
<213> ORGANISM: Deinococcus radiodurans

<400> SEQUENCE: 87

Gly Leu Lys Glu Asn Val Ile Leu Gly Lys Leu Ile Pro Ala
1               5                   10

<210> SEQ ID NO 88
<211> LENGTH: 5
<212> TYPE: PRT
<213> ORGANISM: Deinococcus radiodurans

<400> SEQUENCE: 88

Ser Ile Ile Thr Gln
1               5

<210> SEQ ID NO 89
<211> LENGTH: 28
<212> TYPE: PRT
<213> ORGANISM: Deinococcus radiodurans

<400> SEQUENCE: 89

Met Glu Val Trp Ala Leu Glu Ala Tyr Gly Ala Ala His Val Leu Gln
1               5                   10                  15

Glu Met Leu Thr Ile Lys Ser Asp Asp Ile Asp Gly
            20                  25

<210> SEQ ID NO 90
<211> LENGTH: 13
<212> TYPE: PRT
<213> ORGANISM: Deinococcus radiodurans

<400> SEQUENCE: 90

Thr Ile Pro Glu Ser Phe Lys Val Leu Val Lys Glu Leu
1               5                   10

<210> SEQ ID NO 91
<211> LENGTH: 7
<212> TYPE: PRT
<213> ORGANISM: Thermus thermophilus

<400> SEQUENCE: 91

Leu Leu Gly Lys Arg Val Asp
1               5

<210> SEQ ID NO 92
<211> LENGTH: 14
<212> TYPE: PRT
<213> ORGANISM: Thermus thermophilus

<400> SEQUENCE: 92

Gly Leu Lys Glu Asn Val Ile Leu Gly Arg Leu Ile Pro Ala
1               5                   10

<210> SEQ ID NO 93
<211> LENGTH: 5
<212> TYPE: PRT
<213> ORGANISM: Thermus thermophilus

<400> SEQUENCE: 93

Ser Leu Ile Thr Gln
1               5
```

-continued

```
<210> SEQ ID NO 94
<211> LENGTH: 28
<212> TYPE: PRT
<213> ORGANISM: Thermus thermophilus

<400> SEQUENCE: 94

Met Glu Val Trp Ala Leu Glu Ala Tyr Gly Ala Ala His Thr Leu Gln
1               5                   10                  15

Glu Met Leu Thr Ile Lys Ser Asp Asp Ile Glu Gly
            20                  25

<210> SEQ ID NO 95
<211> LENGTH: 13
<212> TYPE: PRT
<213> ORGANISM: Thermus thermophilus

<400> SEQUENCE: 95

Ser Val Pro Glu Ser Phe Arg Val Leu Val Lys Glu Leu
1               5                   10

<210> SEQ ID NO 96
<211> LENGTH: 7
<212> TYPE: PRT
<213> ORGANISM: Thermus aquaticus

<400> SEQUENCE: 96

Leu Leu Gly Lys Arg Val Asp
1               5

<210> SEQ ID NO 97
<211> LENGTH: 14
<212> TYPE: PRT
<213> ORGANISM: Thermus aquaticus

<400> SEQUENCE: 97

Gly Leu Lys Glu Asn Val Ile Leu Gly Arg Leu Ile Pro Ala
1               5                   10

<210> SEQ ID NO 98
<211> LENGTH: 5
<212> TYPE: PRT
<213> ORGANISM: Thermus aquaticus

<400> SEQUENCE: 98

Ser Ile Ile Thr Gln
1               5

<210> SEQ ID NO 99
<211> LENGTH: 28
<212> TYPE: PRT
<213> ORGANISM: Thermus aquaticus

<400> SEQUENCE: 99

Met Glu Val Trp Ala Leu Glu Ala Tyr Gly Ala Ala His Thr Leu Gln
1               5                   10                  15

Glu Met Leu Thr Leu Lys Ser Asp Asp Ile Glu Gly
            20                  25

<210> SEQ ID NO 100
<211> LENGTH: 13
<212> TYPE: PRT
<213> ORGANISM: Thermus aquaticus

<400> SEQUENCE: 100
```

Ser Val Pro Glu Ser Phe Arg Val Leu Val Lys Glu Leu
1               5                   10

<210> SEQ ID NO 101
<211> LENGTH: 7
<212> TYPE: PRT
<213> ORGANISM: Homo sapiens

<400> SEQUENCE: 101

Met Met Gly Lys Arg Val Asp
1               5

<210> SEQ ID NO 102
<211> LENGTH: 14
<212> TYPE: PRT
<213> ORGANISM: Homo sapiens

<400> SEQUENCE: 102

Ser Pro Ser Ala Cys Leu Val Val Gly Lys Val Val Arg Gly
1               5                   10

<210> SEQ ID NO 103
<211> LENGTH: 5
<212> TYPE: PRT
<213> ORGANISM: Homo sapiens

<400> SEQUENCE: 103

Asp Arg Val Thr Asn
1               5

<210> SEQ ID NO 104
<211> LENGTH: 28
<212> TYPE: PRT
<213> ORGANISM: Homo sapiens

<400> SEQUENCE: 104

Met Glu Arg Asp Ala Leu Leu Ala His Gly Thr Ser Phe Leu Leu His
1               5                   10                  15

Asp Arg Leu Phe Asn Cys Ser Asp Arg Ser Val Ala
            20                  25

<210> SEQ ID NO 105
<211> LENGTH: 13
<212> TYPE: PRT
<213> ORGANISM: Homo sapiens

<400> SEQUENCE: 105

Ser Val Pro Tyr Val Phe Arg Tyr Phe Val Ala Glu Leu
1               5                   10

<210> SEQ ID NO 106
<211> LENGTH: 7
<212> TYPE: PRT
<213> ORGANISM: Homo sapiens

<400> SEQUENCE: 106

Leu Met Gly Lys Arg Val Asp
1               5

<210> SEQ ID NO 107
<211> LENGTH: 14
<212> TYPE: PRT
<213> ORGANISM: Homo sapiens

<400> SEQUENCE: 107

```
Gly Val Ser Glu Asn Ile Met Leu Gly Gln Leu Ala Pro Ala
1               5                   10
```

<210> SEQ ID NO 108
<211> LENGTH: 5
<212> TYPE: PRT
<213> ORGANISM: Homo sapiens

<400> SEQUENCE: 108

```
Gln Ile Leu Asn Arg
1               5
```

<210> SEQ ID NO 109
<211> LENGTH: 28
<212> TYPE: PRT
<213> ORGANISM: Homo sapiens

<400> SEQUENCE: 109

```
Met Glu Arg Asp Cys Gln Ile Ala His Gly Ala Ala Gln Phe Leu Arg
1               5                   10                  15

Glu Arg Leu Phe Glu Ala Ser Asp Arg Tyr Gln Val
            20                  25
```

<210> SEQ ID NO 110
<211> LENGTH: 13
<212> TYPE: PRT
<213> ORGANISM: Homo sapiens

<400> SEQUENCE: 110

```
Arg Met Pro Tyr Ala Cys Lys Leu Leu Phe Gln Glu Leu
1               5                   10
```

<210> SEQ ID NO 111
<211> LENGTH: 7
<212> TYPE: PRT
<213> ORGANISM: Homo sapiens

<400> SEQUENCE: 111

```
Leu Ser Gly Lys Arg Val Asp
1               5
```

<210> SEQ ID NO 112
<211> LENGTH: 14
<212> TYPE: PRT
<213> ORGANISM: Homo sapiens

<400> SEQUENCE: 112

```
Gly Val Ser Glu Cys Ile Ile Met Gly Ile Pro Met Asn Ile
1               5                   10
```

<210> SEQ ID NO 113
<211> LENGTH: 5
<212> TYPE: PRT
<213> ORGANISM: Homo sapiens

<400> SEQUENCE: 113

```
Ala Val Leu Thr Arg
1               5
```

<210> SEQ ID NO 114
<211> LENGTH: 28
<212> TYPE: PRT
<213> ORGANISM: Homo sapiens

<400> SEQUENCE: 114

Met Glu Arg Asp Cys Leu Ile Gly Tyr Gly Ala Ser Met Leu Leu
1               5                   10                  15

Glu Arg Leu Met Ile Ser Ser Asp Ala Phe Glu Val
            20                  25

<210> SEQ ID NO 115
<211> LENGTH: 13
<212> TYPE: PRT
<213> ORGANISM: Homo sapiens

<400> SEQUENCE: 115

Arg Ile Pro Tyr Ala Cys Lys Leu Leu Phe Gln Glu Leu
1               5                   10

<210> SEQ ID NO 116
<211> LENGTH: 54
<212> TYPE: PRT
<213> ORGANISM: Artificial sequence
<220> FEATURE:
<223> OTHER INFORMATION: oligonucleotide primer

<400> SEQUENCE: 116

Gly Cys Gly Thr Cys Cys Thr Cys Thr Gly Ala Ala Thr Cys Thr
1               5                   10                  15

Thr Thr Gly Gly Cys Cys Gly Ala Cys Ala Thr Gly Ala Thr Cys Ala
            20                  25                  30

Ala Ala Gly Gly Thr Ala Ala Cys Ala Gly Gly Thr Cys Gly
        35                  40                  45

Thr Thr Thr Cys Cys Gly
        50

<210> SEQ ID NO 117
<211> LENGTH: 54
<212> TYPE: PRT
<213> ORGANISM: Artificial sequence
<220> FEATURE:
<223> OTHER INFORMATION: oligonucleotide primers

<400> SEQUENCE: 117

Gly Gly Thr Ala Ala Ala Cys Ala Gly Gly Thr Cys Thr Thr
1               5                   10                  15

Thr Cys Cys Gly Thr Cys Ala Gly Ala Ala Cys Cys Thr Gly Cys Thr
            20                  25                  30

Cys Gly Gly Thr Ala Ala Gly Cys Gly Thr Gly Thr Gly Ala Cys
        35                  40                  45

Thr Ala Cys Thr Cys Cys
    50

<210> SEQ ID NO 118
<211> LENGTH: 47
<212> TYPE: PRT
<213> ORGANISM: Artificial sequence
<220> FEATURE:
<223> OTHER INFORMATION: oligonucelotide primer

<400> SEQUENCE: 118

Cys Gly Gly Thr Ala Ala Gly Cys Gly Thr Gly Thr Gly Ala Cys
1               5                   10                  15

Thr Ala Cys Thr Cys Cys Gly Gly Thr Cys Gly Thr Thr Cys Thr Gly
            20                  25                  30

Thr Ala Ala Thr Cys Ala Cys Cys Gly Thr Ala Gly Gly Thr Cys
        35                  40                  45

<210> SEQ ID NO 119
<211> LENGTH: 35
<212> TYPE: PRT
<213> ORGANISM: Artificial sequence
<220> FEATURE:
<223> OTHER INFORMATION: oligonucleotide primer

<400> SEQUENCE: 119

Thr Gly Cys Ala Cys Cys Gly Ala Cys Thr Cys Gly Cys Ala Cys
1               5                   10                  15

Cys Gly Thr Cys Thr Gly Gly Thr Ala Thr Cys Cys Ala Gly Gly
                20                  25                  30

Cys Ala Thr
        35

<210> SEQ ID NO 120
<211> LENGTH: 66
<212> TYPE: PRT
<213> ORGANISM: Artificial sequence
<220> FEATURE:
<223> OTHER INFORMATION: oligonucleotide primer

<400> SEQUENCE: 120

Gly Gly Thr Gly Ala Cys Cys Ala Gly Thr Gly Gly Cys Thr Gly
1               5                   10                  15

Thr Thr Cys Ala Cys Gly Thr Ala Cys Cys Gly Cys Thr Gly Ala Cys
                20                  25                  30

Gly Cys Thr Gly Gly Ala Ala Gly Cys Cys Cys Ala Gly Cys Thr Gly
        35                  40                  45

Gly Ala Ala Gly Cys Gly Cys Gly Thr Gly Cys Gly Cys Thr Gly Ala
    50                  55                  60

Thr Gly
65

<210> SEQ ID NO 121
<211> LENGTH: 61
<212> TYPE: PRT
<213> ORGANISM: Artificial sequence
<220> FEATURE:
<223> OTHER INFORMATION: oligonucleotide primer

<400> SEQUENCE: 121

Gly Cys Gly Ala Ala Cys Thr Cys Gly Gly Thr Thr Ala Cys Cys
1               5                   10                  15

Thr Gly Ala Cys Thr Cys Gly Thr Cys Gly Thr Cys Thr Gly Gly Thr
                20                  25                  30

Thr Gly Ala Cys Gly Thr Gly Gly Cys Gly Cys Ala Gly Gly Ala Cys
        35                  40                  45

Cys Thr Gly Gly Thr Gly Gly Thr Thr Ala Cys Cys Gly
    50                  55                  60

<210> SEQ ID NO 122
<211> LENGTH: 56
<212> TYPE: PRT
<213> ORGANISM: Artificial sequence
<220> FEATURE:
<223> OTHER INFORMATION: oligonucleotide primer

<400> SEQUENCE: 122

Cys Ala Ala Cys Ala Ala Gly Gly Gly Thr Gly Ala Ala Gly Cys Ala
1               5                   10                  15

```
Ala Thr Cys Gly Gly Thr Gly Thr Thr Ala Thr Cys Gly Cys Gly
            20                  25                  30

Cys Ala Cys Ala Gly Thr Cys Cys Ala Thr Cys Gly Thr Gly Ala
        35                  40                  45

Ala Cys Cys Gly Gly Thr Ala
        50              55

<210> SEQ ID NO 123
<211> LENGTH: 46
<212> TYPE: PRT
<213> ORGANISM: Artificial sequence
<220> FEATURE:
<223> OTHER INFORMATION: oligonuceltide primer

<400> SEQUENCE: 123

Ala Ala Cys Cys Gly Ala Gly Thr Cys Thr Thr Cys Ala Thr Cys
1               5                   10                  15

Thr Cys Cys Gly Cys Gly Gly Cys Ala Thr Cys Gly Thr Thr Cys Cys
            20                  25                  30

Ala Gly Gly Ala Gly Ala Cys Cys Ala Cys Thr Cys Gly Cys
        35                  40                  45

<210> SEQ ID NO 124
<211> LENGTH: 62
<212> TYPE: PRT
<213> ORGANISM: Artificial sequence
<220> FEATURE:
<223> OTHER INFORMATION: oligonucleotide primer

<400> SEQUENCE: 124

Cys Thr Gly Cys Gly Cys Gly Gly Cys Cys Thr Gly Ala Ala Ala Gly
1               5                   10                  15

Ala Gly Ala Ala Cys Gly Thr Thr Ala Thr Cys Gly Thr Gly Gly
            20                  25                  30

Thr Cys Gly Thr Cys Thr Gly Ala Thr Cys Cys Cys Gly Gly Cys Ala
            35                  40                  45

Gly Gly Thr Ala Cys Cys Gly Gly Thr Thr Ala Cys Gly Cys
        50                  55                  60

<210> SEQ ID NO 125
<211> LENGTH: 50
<212> TYPE: PRT
<213> ORGANISM: Artificial sequence
<220> FEATURE:
<223> OTHER INFORMATION: oligonucleotide primer

<400> SEQUENCE: 125

Gly Cys Ala Cys Gly Cys Gly Cys Gly Thr Thr Cys Cys Ala Cys Cys
1               5                   10                  15

Gly Gly Thr Thr Cys Thr Thr Ala Cys Ala Gly Cys Cys Thr Gly Gly
            20                  25                  30

Thr Thr Ala Cys Thr Cys Ala Gly Cys Ala Gly Cys Cys Gly Cys Thr
        35                  40                  45

Gly Gly
    50

<210> SEQ ID NO 126
<211> LENGTH: 38
<212> TYPE: PRT
<213> ORGANISM: Artificial sequence
<220> FEATURE:
<223> OTHER INFORMATION: oligonucleotide primer
```

-continued

```
<400> SEQUENCE: 126

Gly Gly Thr Thr Ala Cys Thr Cys Ala Gly Cys Ala Gly Cys Cys Gly
1               5                   10                  15

Cys Thr Gly Gly Gly Thr Gly Thr Ala Ala Gly Gly Cys Ala Cys
                20                  25                  30

Ala Gly Thr Thr Cys Gly
            35

<210> SEQ ID NO 127
<211> LENGTH: 50
<212> TYPE: PRT
<213> ORGANISM: Artificial sequence
<220> FEATURE:
<223> OTHER INFORMATION: oligonucleotide primer

<400> SEQUENCE: 127

Thr Ala Ala Gly Gly Cys Ala Cys Ala Gly Thr Thr Cys Gly Gly Thr
1               5                   10                  15

Gly Gly Thr Cys Ala Gly Cys Gly Thr Thr Cys Gly Gly Gly
            20                  25                  30

Ala Gly Ala Thr Gly Gly Ala Ala Gly Thr Gly Thr Gly Gly Gly Cys
        35                  40                  45

Gly Cys
    50

<210> SEQ ID NO 128
<211> LENGTH: 53
<212> TYPE: PRT
<213> ORGANISM: Artificial sequence
<220> FEATURE:
<223> OTHER INFORMATION: oligonucleotide primer

<400> SEQUENCE: 128

Gly Gly Ala Ala Gly Thr Gly Thr Gly Gly Cys Gly Cys Thr Gly
1               5                   10                  15

Gly Ala Ala Gly Cys Ala Thr Ala Cys Gly Gly Cys Gly Cys Ala Gly
            20                  25                  30

Cys Ala Thr Ala Cys Ala Cys Cys Thr Gly Cys Ala Gly Gly Ala
        35                  40                  45

Ala Ala Thr Gly Cys
    50

<210> SEQ ID NO 129
<211> LENGTH: 50
<212> TYPE: PRT
<213> ORGANISM: Artificial sequence
<220> FEATURE:
<223> OTHER INFORMATION: oligunucleotide primer

<400> SEQUENCE: 129

Ala Thr Ala Cys Ala Cys Cys Cys Thr Gly Cys Ala Gly Gly Ala Ala
1               5                   10                  15

Ala Thr Gly Cys Thr Cys Ala Cys Cys Gly Thr Thr Ala Ala Gly Thr
            20                  25                  30

Cys Thr Gly Ala Thr Gly Ala Cys Gly Thr Gly Ala Ala Cys Gly Gly
        35                  40                  45

Thr Cys
    50

<210> SEQ ID NO 130
<211> LENGTH: 59
```

```
<212> TYPE: PRT
<213> ORGANISM: Artificial sequence
<220> FEATURE:
<223> OTHER INFORMATION: oligonucleotide primer

<400> SEQUENCE: 130

Gly Thr Cys Thr Gly Ala Thr Gly Ala Cys Gly Thr Gly Ala Ala Cys
1               5                   10                  15

Gly Gly Thr Cys Gly Thr Ala Cys Cys Ala Ala Gly Ala Thr Gly Thr
                20                  25                  30

Ala Thr Ala Ala Ala Ala Ala Cys Ala Thr Cys Gly Thr Gly Gly Ala
            35                  40                  45

Cys Gly Gly Cys Ala Ala Cys Cys Ala Thr Cys
        50                  55

<210> SEQ ID NO 131
<211> LENGTH: 53
<212> TYPE: PRT
<213> ORGANISM: Artificial sequence
<220> FEATURE:
<223> OTHER INFORMATION: oligonucleotide primer

<400> SEQUENCE: 131

Cys Ala Thr Cys Gly Thr Gly Ala Cys Gly Gly Cys Ala Ala Cys
1               5                   10                  15

Cys Ala Thr Cys Ala Gly Ala Thr Gly Gly Ala Gly Cys Cys Gly Gly
                20                  25                  30

Gly Cys Ala Thr Gly Cys Cys Ala Gly Ala Ala Thr Cys Cys Thr Thr
            35                  40                  45

Cys Ala Ala Cys Gly
        50

<210> SEQ ID NO 132
<211> LENGTH: 44
<212> TYPE: PRT
<213> ORGANISM: Artificial sequence
<220> FEATURE:
<223> OTHER INFORMATION: oligonucleotide primer

<400> SEQUENCE: 132

Cys Ala Thr Gly Cys Cys Ala Gly Ala Ala Thr Cys Cys Thr Thr Cys
1               5                   10                  15

Ala Ala Cys Gly Thr Ala Thr Thr Gly Thr Thr Gly Ala Ala Ala Gly
                20                  25                  30

Ala Gly Ala Thr Thr Cys Gly Thr Thr Cys Gly Cys
            35                  40

<210> SEQ ID NO 133
<211> LENGTH: 55
<212> TYPE: DNA
<213> ORGANISM: E. coli

<400> SEQUENCE: 133
aggctttaca ctttatgctt ccggctcgta taatgtgtgg aattgtgagc ggata      55

<210> SEQ ID NO 134
<211> LENGTH: 36
<212> TYPE: DNA
<213> ORGANISM: E. coli

<400> SEQUENCE: 134
aggcttacac tttatgcttc cggctcgtat aatgtg                           36
```

What is claimed is:

1. A method for identifying an agent that binds to a homologous switch-region amino-acid sequence of bacterial RNAP (RNA polymerase) in a first entity, comprising the steps of: (a) preparing a reaction solution including the agent to be tested and a first entity including a homologous switch-region amino-acid sequence of bacterial RNAP; and (b) detecting at least one of the presence, extent, concentration-dependence, or kinetics of binding of the agent to the homologous switch-region amino-acid sequence, wherein the agent is not myxopyronin, corallopyronin or ripostatin.

2. The method of claim 1 wherein the first entity is an intact bacterial RNAP.

3. The method of claim 1 wherein the first entity is *Escherichia coli* RNAP.

4. The method of claim 1 wherein the first entity is *Bacillus subtilis* RNAP.

5. The method of claim 1 further comprising the step of: assessing at least one of the presence, extent, concentration-dependence, or kinetics of binding of the agent to a second entity that contains a derivative of a bacterial RNAP homologous switch-region amino-acid sequence having at least one substitution, insertion, or deletion.

6. The method of claim 5 wherein the second entity is a derivative of an intact bacterial RNAP.

7. The method of claim 5 wherein the second entity is a derivative of *Escherichia coli* RNAP.

8. The method of claim 5 wherein the second entity is a derivative of *Bacillus subtilis* RNAP.

9. The method of claim 1 further comprising comparison of: (a) at least one of the presence, extent, concentration-dependence, or kinetics of binding of the agent to the first entity, and (b) at least one of the presence, extent, concentration-dependence, or kinetics of binding of the agent to a eukaryotic RNAP.

10. The method of claim 9 wherein the eukaryotic RNAP is a human RNAP.

11. The method of claim 9 wherein the eukaryotic RNAP is a human RNAP II.

12. A method for identifying an agent that inhibits an activity of a bacterial RNAP by binding to a homologous switch-region amino-acid sequence of a bacterial RNAP, comprising: (a) preparing a reaction solution comprising the agent to be tested and a first entity containing a homologous switch-region amino-acid sequence of a bacterial RNAP; and (b) detecting at least one of the presence, extent, concentration-dependence, or kinetics of inhibition of an activity of said first entity, wherein inhibition involves binding of the agent to the homologous switch-region amino-acid sequence of the bacterial RNAP, wherein the agent is not myxopyronin, corallopyronin or ripostatin.

13. The method of claim 12 wherein the first entity is an intact bacterial RNAP.

14. The method of claim 12 wherein first entity is *Escherichia coli* RNAP.

15. The method of claim 12 wherein the first entity is *Bacillus subtilis* RNAP.

16. The method of claim 12 wherein the activity is transcription initiation.

17. The method of claim 12 wherein the activity is transcription elongation.

18. The method of claim 12 wherein the activity is σ binding.

19. The method of claim 12 wherein the activity is DNA binding.

20. The method of claim 12 wherein the activity is open-complex formation.

21. The method of claim 12 wherein the activity is RNA synthesis.

22. The method of claim 12 further comprising the step of: assessing at least one of the presence, extent, concentration-dependence, or kinetics of the inhibition by the agent on an activity of a second entity that contains a derivative of a bacterial RNAP homologous switch-region amino-acid sequence having at least one substitution, insertion, or deletion.

23. The method of claim 22 wherein the second entity is a derivative of an intact bacterial RNAP.

24. The method of claim 22 wherein the second entity is a derivative of *Escherichia coli* RNAP.

25. The method of claim 22 wherein the second entity is a derivative of *Bacillus subtilis* RNAP.

26. The method of claim 22 wherein the activity is transcription initiation.

27. The method of claim 22 wherein the activity is transcription elongation.

28. The method of claim 22 wherein the activity is σ binding.

29. The method of claim 22 wherein the activity is DNA binding.

30. The method of claim 22 wherein the activity is open-complex formation.

31. The method of claim 22 wherein the activity is RNA synthesis.

32. The method of claim 22 wherein inhibition of an activity of the first entity and inhibition of an activity of the second entity are assessed sequentially.

33. The method of claim 22 wherein inhibition of an activity of the first entity and inhibition of an activity of the second entity are assessed simultaneously.

34. The method of claim 12 further comprising comparison of: (a) at least one of the presence, extent, concentration-dependence, or kinetics of inhibition by the agent on an activity of the first entity, and (b) at least one of the presence, extent, concentration-dependence, or kinetics of inhibition by the agent on an activity of a eukaryotic RNAP.

35. The method of claim 34 wherein the eukaryotic RNAP is a human RNAP.

36. The method of claim 34 wherein the eukaryotic RNAP is a human RNAP II.

37. The method of claim 12 wherein at least one of the presence, extent, concentration-dependence, or kinetics of inhibition by the agent on an activity of the first entity also is compared to at least one of the presence, extent, concentration-dependence, or kinetics of inhibition by an inhibitory compound specific to the bacterial RNAP homologous switch-region amino-acid sequence of on an activity of the first entity.

38. A method for identifying an agent that binds to a homologous switch-region amino-acid sequence of a bacterial RNAP, comprising (a) preparing a reaction solution comprising the agent to be tested, a reference compound that binds to a homologous switch-region amino-acid sequence of a bacterial RNAP, and a first entity containing a homologous switch-region amino-acid sequence of a bacterial RNAP, and (b) detecting at least one of the presence, extent, concentration-dependence, or kinetics of competition by the agent for binding of the reference compound to the homologous switch-region amino-acid sequence of the bacterial RNAP, wherein the agent is not myxopyronin, corallopyronin or ripostatin.

39. The method of claim 38 wherein the first entity is an intact bacterial RNAP.

40. The method of claim 38 wherein the first entity is *Escherichia coli* RNAP.

41. The method of claim 38 wherein the first entity is *Bacillus subtilis* RNAP.

42. The method of claim 38 wherein the reference compound contains a detectable group.

43. The method of claim 38 wherein the agent contains a chromophore.

44. The method of claim 38 wherein the agent contains a fluorophore.

45. The method of claim 38 wherein the reference compound is a chromophore-labeled inhibitory compound specific to the bacterial RNAP homologous switch-region amino-acid sequence.

46. The method of claim 38 wherein the reference compound is a fluorophore-labeled inhibitory compound specific to the bacterial RNAP homologous switch-region amino-acid sequence.

47. The method of claim 38 further comprising measurement of FRET.

48. The method of claim 38 further comprising the step of: assessing at least one of the presence, extent, concentration-dependence, or kinetics of the binding of the agent to a second entity that contains a derivative of a bacterial RNAP homologous switch-region amino-acid sequence having at least one substitution, insertion, or deletion.

49. The method of claim 48 wherein the second entity is a derivative of an intact bacterial RNAP.

50. The method of claim 48 wherein the second entity is a derivative of *Escherichia coli* RNAP.

51. The method of claim 48 wherein the second entity is a derivative of *Bacillus subtilis* RNAP.

52. The method of claim 38 further comprising comparison of: (a) at least one of the presence, extent, concentration-dependence, or kinetics of binding of the agent to the first entity, and (b) at least one of the presence, extent, concentration-dependence, or kinetics of binding of the agent to a eukaryotic RNAP.

53. The method of claim 52 wherein the eukaryotic RNAP is a human RNAP.

54. The method of claim 52 wherein the eukaryotic RNAP is a human RNAP II.

55. The method of claim 38 wherein at least one of the presence, extent, concentration-dependence, or kinetics of binding of the agent to the first entity is compared to at least one of the presence, extent, concentration-dependence, or kinetics of binding of an inhibitory compound specific to the bacterial RNAP homologous switch-region amino-acid sequence to the first entity.

* * * * *